United States Patent [19]
Li et al.

[11] Patent Number: 5,858,065
[45] Date of Patent: Jan. 12, 1999

[54] PROCESS AND SYSTEM FOR SEPARATION AND RECOVERY OF PERFLUOROCOMPOUND GASES

[75] Inventors: Yao-En Li, Buffalo Grove; Joseph E. Paganessi, Burr Ridge; David Vassallo, Glenview, all of Ill.; Gregory K. Fleming, Wilmington, Del.

[73] Assignee: American Air Liquide, Walnut Creek, Calif.

[21] Appl. No.: 783,949

[22] Filed: Jan. 16, 1997

Related U.S. Application Data

[63] Continuation-in-part of Ser. No. 665,142, Jun. 14, 1996.
[51] Int. Cl.[6] .................................................. B01D 53/22
[52] U.S. Cl. .......................... 95/45; 95/47; 95/90; 95/92; 95/230; 95/237; 96/4; 96/8; 96/108; 96/134
[58] Field of Search ................................ 95/45, 47–49, 95/51–54, 90, 92, 149, 230, 237; 96/4, 7–14, 108, 134

[56] References Cited

U.S. PATENT DOCUMENTS

| | | | |
|---|---|---|---|
| 2,947,687 | 8/1960 | Lee | 210/23 |
| 2,953,502 | 9/1960 | Binning et al. | 202/42 |
| 2,960,462 | 11/1960 | Lee et al. | 208/308 |
| 2,970,106 | 1/1961 | Binning et al. | 208/347 |
| 3,508,994 | 4/1970 | Nyrop | 156/280 |
| 3,616,607 | 11/1971 | Klass et al. | 55/16 |
| 3,648,845 | 3/1972 | Riley | 210/490 |
| 4,086,310 | 4/1978 | Bottenbruch et al. | 264/41 |
| 4,113,628 | 9/1978 | Alegranti | 210/500 |
| 4,132,824 | 1/1979 | Kimura et al. | 428/220 |
| 4,155,793 | 5/1979 | Salemme et al. | 156/246 |
| 4,156,597 | 5/1979 | Browall | 55/16 |
| 4,178,224 | 12/1979 | Porter | 204/237 |
| 4,192,824 | 3/1980 | Robinson et al. | 585/409 |
| 4,378,324 | 3/1983 | Makino et al. | 264/41 |
| 4,424,067 | 1/1984 | Tarasenko et al. | 55/16 |

(List continued on next page.)

FOREIGN PATENT DOCUMENTS

| | | |
|---|---|---|
| 0 239 190 A2 | 9/1987 | European Pat. Off. . |
| 0 358 915 A2 | 3/1990 | European Pat. Off. . |
| 60-022902 | 2/1985 | Japan . |
| 61-187918 | 8/1986 | Japan . |
| 40-16213 | 1/1992 | Japan . |
| 43-22716 | 11/1992 | Japan . |
| WO 90/15662 | 12/1990 | WIPO . |

OTHER PUBLICATIONS

Michel T. Mocella, *Perfluorocompound Emission Reduction from Semiconductor Processing Tools: An Overview of Options and Strategies*, Global Warming Symposium, Dallas, TX., Jun. 7–8, 1994.

Larry Anderson, *Vector Technology's Phoenix Combustor*, Global Warning Symposium, Dallas, TX. Jun. 7–8, 1994.

AT&T Microelectronics and Novapure Corp., *PFC Concentration and Recycle*, Global Warming Symposium, Dallax TX., Jun. 7–8, 1994.

Air Liquide America Corporation, *SOLVAL™ Solvent Condensation and Recovery System*, Technical Bulletin, 1994.

(List continued on next page.)

*Primary Examiner*—Robert Spitzer
*Attorney, Agent, or Firm*—Burns, Doane, Swecker & Mathis, L.L.P.

[57] ABSTRACT

Processes and systems to recover at least one perfluorocompound gas from a gas mixture are provided. In one embodiment the inventive process comprises providing a gas mixture comprising at least one perfluorocompound gas and at least one carrier gas, the gas mixture being at a predetermined pressure; providing at least one size selective membrane having a feed side and a permeate side; contacting the feed side of the at least one membrane with the gas mixture; withdrawing from the feed side of the membrane as a non-permeate stream at a pressure which is substantially equal to the predetermined pressure a concentrated gas mixture comprising essentially the at least one perfluorocompound gas; and withdrawing from the permeate side of the membrane as a permeate stream a depleted gas mixture comprising essentially the at least one carrier gas.

77 Claims, 13 Drawing Sheets

U.S. PATENT DOCUMENTS

| | | | |
|---|---|---|---|
| 4,460,526 | 7/1984 | Makino et al. | 264/41 |
| 4,474,662 | 10/1984 | Makino et al. | 210/500.2 |
| 4,485,056 | 11/1984 | Makino et al. | 264/41 |
| 4,512,893 | 4/1985 | Makino et al. | 210/500.2 |
| 4,553,983 | 11/1985 | Baker | 55/16 |
| 4,602,922 | 7/1986 | Cabasso et al. | 55/158 |
| 4,664,669 | 5/1987 | Ohyabu et al. | 623/66 |
| 4,689,267 | 8/1987 | Takamizawa et al. | 428/376 |
| 4,701,187 | 10/1987 | Choe et al. | 55/16 |
| 4,713,292 | 12/1987 | Takemura et al. | 428/373 |
| 4,714,481 | 12/1987 | Matsuura et al. | 55/158 |
| 4,717,394 | 1/1988 | Hayes | 55/16 |
| 4,718,921 | 1/1988 | Makino et al. | 95/52 |
| 4,741,829 | 5/1988 | Takemura et al. | 210/500.23 |
| 4,743,435 | 5/1988 | Kitahara et al. | 423/210 |
| 4,756,932 | 7/1988 | Puri | 427/175 |
| 4,784,837 | 11/1988 | Kitayama et al. | 423/210 |
| 4,826,599 | 5/1989 | Bikson et al. | 210/500.3 |
| 4,880,441 | 11/1989 | Kesting et al. | 55/16 |
| 4,881,953 | 11/1989 | Prasad et al. | 55/16 |
| 4,910,001 | 3/1990 | Kitahara et al. | 423/210 |
| 4,941,893 | 7/1990 | Hsieh et al. | 55/16 |
| 4,957,893 | 9/1990 | St. Hilaire | 55/16 |
| 4,988,371 | 1/1991 | Jeanes et al. | 55/16 |
| 4,996,030 | 2/1991 | Kitahara et al. | 423/210 |
| 5,009,869 | 4/1991 | Weinberg et al. | 95/50 X |
| 5,051,114 | 9/1991 | Nemser et al. | 55/16 |
| 5,064,447 | 11/1991 | Lee | 55/16 |
| 5,085,676 | 2/1992 | Ekiner et al. | 55/158 |
| 5,182,088 | 1/1993 | Leondaridis et al. | 423/210 |
| 5,196,616 | 3/1993 | Lee et al. | 570/178 |
| 5,205,842 | 4/1993 | Prasad | 95/52 X |
| 5,240,471 | 8/1993 | Barbe et al. | 95/54 |
| 5,256,295 | 10/1993 | Baker et al. | 210/640 |
| 5,259,869 | 11/1993 | Auvil et al. | 95/52 |
| 5,281,253 | 1/1994 | Thompson | 95/22 |
| 5,281,255 | 1/1994 | Toy et al. | 95/50 |
| 5,282,964 | 2/1994 | Young et al. | 210/321.8 |
| 5,282,969 | 2/1994 | Xu | 210/640 |
| 5,290,341 | 3/1994 | Barbe | 95/54 |
| 5,308,382 | 5/1994 | Prasad | 95/52 X |
| 5,378,439 | 1/1995 | Delobel et al. | 423/210 |
| 5,383,956 | 1/1995 | Prasad et al. | 95/52 X |
| 5,383,957 | 1/1995 | Barbe et al. | 96/8 |
| 5,417,742 | 5/1995 | Tamhankar et al. | 95/96 |
| 5,502,969 | 4/1996 | Jin et al. | 62/11 |
| 5,605,564 | 2/1997 | Collins | 95/52 |

OTHER PUBLICATIONS

Shan–Tao Hsieh and George E. Keller II, Separation of Hydrogen from Silane via Membranes: A Step in the Production of Ultra–High–Purity Silicon, Journal of Membrane Science, 70 (1992), pp. 143–152.

Carson, William M., Christian, Kimberly A., Crossland, Eugene C., Hsiung, Thomas H., Ridgeway, Robert G., and Yang, James H. "Large Scale PFC Capture System". Air Products and Chemicals, Inc. presented at Semicon Southwest, Austin, TX. Oct. 13, 1997.

Norton, Francis, J. "Gas Permeation Through Lexan Polycarbonate Resin". General Electric Research Laboratory. Journal of Applied Polymer Science vol. 7, pp. 1649–1659 (1963).

Stannett, V. and Williams, J.L. "The Permeability of Poly-(ethyl Methacrylate) to Gases and Water Vapor". Camille Dreyfus Laboratory. Journal of Polymer Science: Part C, No. 10, pp. 45–49 (1965).

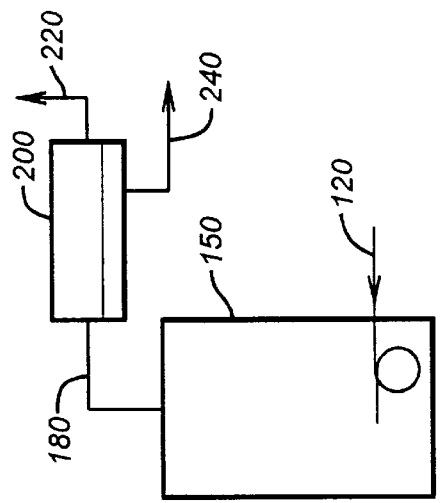
FIG. 13
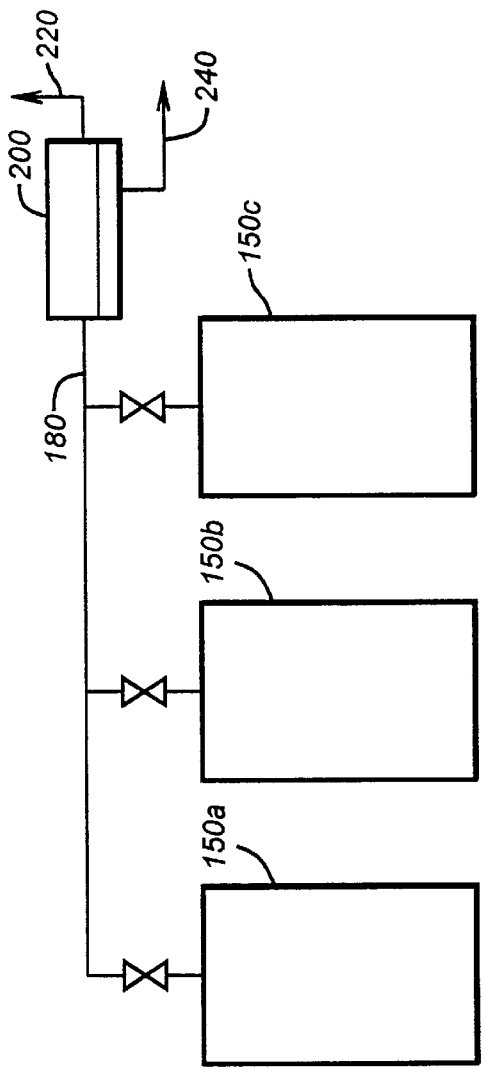
FIG. 14
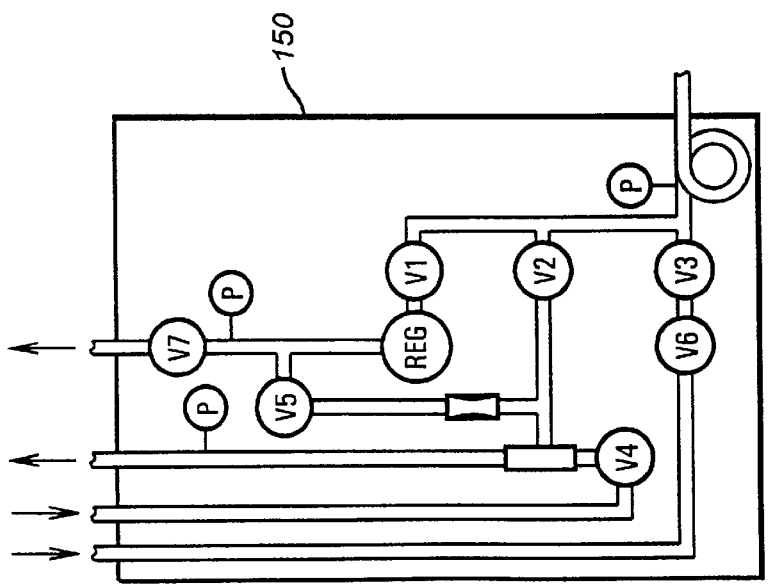
(PRIOR ART) FIG. 12

PROCESS AND SYSTEM FOR SEPARATION AND RECOVERY OF PERFLUOROCOMPOUND GASES

CROSS-REFERENCE TO RELATED APPLICATIONS

This application is a continuation-in-part of copending application Ser. No. 08/665,142, filed Jun. 14, 1996.

FIELD OF THE INVENTION

The invention relates to gas separation processes and more particularly the separation and recovery (or disposal) of perfluorocompound gases from a gas mixture. Especially, the invention relates to concentrating low concentration gas mixtures comprising perfluorocompound gases such as those present in the effluent of a semiconductor manufacturing process, particularly the etching and cleaning steps.

BACKGROUND OF THE INVENTION

The semiconductor industry uses perfluorocompounds such as $CF_4$, $C_2F_6$, $C_3F_8$, $C_4F_{10}$, $CHF_3$, $SF_6$, $NF_3$, and the like, in semiconductor manufacturing processes involving gases, particularly in various etching steps of the semiconductor manufacturing processes as well as in the chamber cleaning step of the manufacturing process. Such perfluorocompound gases are used either pure or diluted, for example with air or nitrogen or other inert gas or in admixture with other perfluorocompound gases or other carrier gases (for example inert gases). All of the perfluorocompound gases do not necessarily react with other species during the manufacturing processes. Further, when reactors are cleaned or evacuated to carry out another step of the manufacturing process, the effluent gases or gas mixtures are preferably not vented, even if they are largely diluted with air or any other gas such as inert gas. Most of the perfluorocompounds (also called "PFCs") have lifetimes measured in thousands of years in the atmosphere and are also strong infrared absorbers. In the "Global Warming Symposium" held on Jun. 7–8, 1994, in Dallas, Tex., U.S.A., carbon tetrafluoride ($CF_4$), hexafluoroethane ($C_2F_6$), nitrogen trifluoride ($NF_3$), and sulfur hexafluoride ($SF_6$) were identified as "greenhouse gases" of concern to the semiconductor industry.

In a presentation made at the above symposium by Michael T. Mocella entitled "Perfluorocompound Emission Reduction From Semiconductor Processing Tools: An Overview Of Options And Strategies", various possible strategies to control emission of these gases in the atmosphere were presented.

Apart from process replacement by non PFCs, several methods are already known or under development:

chemical-thermal decomposition with various activated metals wherein the spent bed material must be disposed. This method is presently considered commercially promising but unproven technology.

combustion-based decomposition process (or chemical-thermal process) using a flame to supply both the thermal energy, and the reactants for the decomposition. Here, there are some safety issues associated with the hydrogen or natural gas fuels used and all the PFCs will produce hydrofluoric acid (HF) as a combustion product (if the temperature is high enough), whose emissions must also be abated. It was suggested that decomposition temperatures may also be generated using a resistance heater.

plasma-based decomposition process which involves the use of a plasma such as coupled radio frequency systems to partially decompose $C_2F_6$, with over 90% decomposition of $C_2F_6$. However, such systems are not yet commercially proven. Oxygen is usually needed to drive the decomposition to non PFC products, and the problematic generation of HF would be present.

recovery process wherein the PFCs are recovered instead of being destroyed in order to be recycled. This kind of process is of a great interest because it is considered as an environmentally responsible approach. Different schemes were suggested as possible "based on combinations of adsorption or low temperature trapping of PFCs". There are, however, several challenges such as dealing with the large amount of nitrogen associated with the pump operation, the close boiling points of $CF_4$ and $NF_3$, the mixing, of various process streams and/or possible reactions with adsorbents. While recycle was suggested, there are obvious questions about recycling such mixtures.

Another combustion system for destroying high nitrogen content effluent gas streams comprising PFCs is disclosed in an article entitled "Vector Technology's Phoenix Combustor" by Larry Anderson also presented at the same symposium Jun. 7–8, 1994. This abatement system also uses a gas flame (natural gas or hydrogen with air), which leads then to the same problem of HF generation together with the need for further destruction (plus the Generation of $NO_x$, $CO_2$ inherent to any combustion process).

In the article presented at the same symposium Jun. 7–8, 1994 by AT&T Microelectronics and Novapure Corporation entitled "PFC Concentration and Recycle", the authors acknowledge the advantages of the recovery processes which avoid production of carbon dioxide, $NO_x$, and HF (compared to combustion processes). The process disclosed the use of a dual bed adsorber (activated carbon), wherein one of the beds is in the adsorption mode, while the second bed is regenerated: the PFCs are adsorbed on the carbon sieves while the "carrier" gases, such as nitrogen, hydrogen are not adsorbed and are vented to the exhaust system. When the system is switched on the second adsorber, the first adsorber is evacuated using a vacuum pump, and the effluent is recompressed and the PFC gas mixture is recovered. One of the issues not yet resolved with such a system is that $CF_4$, which is non polar, is not readily adsorbed by the carbon sieve, but is then rejected with the vent gases. Also, any adsorption system is very sensitive to moisture and any trace of water has to be removed from the feed flow.

It is known from U.S. Pat. No. 5,281,255 incorporated herein by reference, to use membranes made of rubbery polymers such as poly dimethyl siloxane or certain particular polymers such as a substituted polyacethylene to recover condensable organic components having a boiling point higher than −50° C., essentially hydrocarbons ($CH_4$, $C_2H_6$, and the like), said hydrocarbons having the property of permeating through said membranes much faster than air, and then recovering on the permeate side of the membrane said hydrocarbons. The permeate (hydrocarbons) is then recovered at either substantially atmospheric pressure or lower pressure while the non-permeate (e.g. $N_2$) remains at the feed pressure and is vented. However, by this approach, all of the pressure energy of the feed stream is lost.

Also, it is disclosed in WO 90/15662, published Dec. 27, 1990, a selectively permeable membrane formed from an amorphous polymer of perfluoro 2-2 dimethyl 1-3-dioxole which is useful in the separation of hydrocarbons or chlorofluorocarbons from, for example, air. Such a particular membrane apparently permeates oxygen and nitrogen faster than hydrocarbons and chlorofluorocarbons which can be recovered unexpectedly on the non-permeate side of the membrane, contrary to all of the membranes, including those disclosed in U.S. Pat. Nos. 4,553,983 and 5,281,255. In this PCT application, there is also disclosed a mixture of the amorphous polymer of perfluoro 2-2 dimethyl 1-3 dioxole and polytetrafluoroethylene. All these perfluoro polymers are known to be resistant to most of the harmful chlorofluorocarbons and hydrocarbons which might suggest their commercial suitability for such separation. However, such polymer is not well suited for PFC recovery, having only limited utility at low concentration.

There exists a need for an environmentally sound process for concentration and/or recovery of PFCs from a gaseous stream, which can be used with a feed flow comprising or saturated with, moisture, which can safely handle recovery and/or concentration of PFC's even with important or extreme variations of flows and/or concentration and which does not produce hydrofluoric acid (HF) as a by product.

SUMMARY OF THE INVENTION

It has now been unexpectedly found that effluent gases, for example, from a semiconductor manufacturing process, which comprise perfluorocompounds can be treated efficiently by using certain, preferably hollow fiber, membranes which permeate much faster the "carrier gases" of the effluent gas mixture, such as air, nitrogen, oxygen, argon and/or helium, than the PFCs of the gas mixture which are then recovered on the non-permeate side of the membrane.

One aspect of the invention relates to a process to recover at least one perfluorocompound gas from a gas mixture, comprising the steps of
 a) providing a gas mixture comprising at least one perfluorocompound gas and at least one carrier gas, the gas mixture being at a predetermined pressure;
 b) providing at least one membrane having a feed side and a permeate side, the membrane exhibiting preferential permeation of at least one carrier gas and being relatively non-permeable to at least one perfluorocompound gaseous species and for which selectivity SEL is greater than 1.0.
  wherein, SEL is $[D_c] [S_c]/[D_p] [S_p]$
   $D_p$ is the mobility selectivity of a perfluorocompound gas
   $S_p$ is the solubility selectivity of the perfluorocompound gas
   $D_c$ is the mobility selectivity of a carrier gas
   $S_c$ is the solubility selectivity of the carrier gas
 c) contacting the feed side of the at least one membrane with the gas mixture;
 d) withdrawing from the feed side of the membrane as a first non-permeate stream at a pressure which is substantially equal to the predetermined pressure, a concentrated gas mixture comprising essentially at least one perfluorocompound gas, and
 e) withdrawing from the permeate side of at least one membrane as a permeate stream a depleted gas mixture consisting essentially of the at least one carrier gas.

Preferred membranes are glassy polymeric membranes, more preferably asymmetric or composite membranes. Preferably, glassy polymeric membranes most useful do not include perfluorinated membranes. However, the glassy polymeric membranes used in accordance with the invention can comprise a layer, including a posttreatment layer as disclosed in U.S. Ser. No. 08/138,309 filed Oct. 21, 1993, and which is incorporated herein by reference, made of a fluorinated polymer such as polytetrafluoroethylene, amorphous perfluoro 2-2 dimethyl 1-3 dioxide, and the like.

According to another aspect, the invention also relates to a process to recover a perfluorocompound gas or gas mixture derived from a semiconductor manufacturing process. In this aspect, the invention comprises the steps of pretreating the gas mixture to substantially remove components (acid gases, silanes, particles, and the like) which are harmful to the membrane and delivering a pretreated gas mixture to at least one size selective membrane having a feed side and a permeate side, contacting the feed side of the membrane with the pretreated gas mixture at a first pressure, withdrawing in the residue the perfluorocompound gas or gas mixture at a pressure which is substantially equal to the first pressure and withdrawing a permeate gas at a second pressure which is lower than the first pressure from the permeate side of the membrane. The semiconductor manufacturing process using PFCs may be selected from etching processes including oxide, metal and dielectric; deposition processes including silicon CVD, tungsten backetching, dry chamber cleaning, and the like.

Some of the size selective membranes used in this invention are sensitive to, and may be harmed by certain harmful by-products, i.e. harmful components which may alter via coating or chemical or morphological modification. It is accordingly preferred to treat the gas mixture to remove or treat these compounds prior to introduction to the membrane. Preferably all species in the feed flow stream which are potentially harmful to the membrane are removed by scrubbing, adsorption or chemical reactive capture means, including harmful gaseous HF, $NH_3$, $WF_6$, $O_3$, $BCl_3$; corrosive species; any pyrophoric-species including silicon hydrides such as $SiH_4$; particulates having average diameter greater than about 20 micrometers, and any oil mists. Additionally, it is preferred that compressors used in the methods and systems of the invention be sealed and oil-free.

One preferred aspect of the invention relates to a process to recover at least one perfluorocompound gas or gas mixture, comprising the steps of:
 a) providing a glassy polymer membrane having a feed side and a permeate side;
 b) providing a gas mixture at a first pressure comprising at least one perfluorocompound gaseous species, at least one harmful species for the membrane, and at least one carrier gas;
 c) treating said gas mixture with a dry scrubber and/or wet scrubber, or contacting in scrubber means to substantially remove species harmful to said membrane and reduce the concentration of said harmful species to an acceptable level for said membrane resulting in a scrubbed gas mixture at a second pressure;
 d) contacting the feed side of said membrane with said scrubbed gas mixture at substantially said second pressure or at a higher pressure;
 e) withdrawing a concentrated gas mixture comprising a higher concentration of the at least one perfluorocompound gas, relative to the scrubbed gas mixture, from the feed side of the membrane as a non-permeate stream at a pressure which is substantially equal to said second pressure, and
 f) withdrawing a depleted gas or gas mixture from the permeate side of said membrane as a permeate stream which is enriched in a carrier gas and depleted in the at least one perfluorocompound.

According to a preferred aspect of the invention, after concentrating the PFCs with a membrane, the various PFCs are separated from each other by a process such as selective condensation or adsorption in order to recover either separate PFCs or mixtures of PFCs having close boiling points. According to another aspect of the invention, the PFCs gas mixture is concentrated again, for example, with a second membrane, or the PFCs gas mixture is stored or recycled in the process (with or without additional treatment).

Other preferred process and system aspects of the invention include provision of a vacuum pump, heat exchanger, compressor, or cryogenic pump in order that the PFC gas mixture may be compressed, at least partially liquefied, and stored for future use. Another feature of the invention includes concentrating the PFC gas mixture using a plurality of membranes arranged in series, with the possibility of the concentrated PFC gas mixture from each membrane unit being capable of use as a sweep gas of the permeate side of any one of or all of the membrane units in the series. A further aspect of the invention is the provision of a PFC gas mixture surge tank prior to recycling the PFCs to the semiconductor manufacturing process, or prior to being fractionated and purified by cryogenic adsorption or other means, or routed to storage.

Another aspect of the invention is a semiconductor manufacturing system comprising:

a) at least one reactor chamber adapted to receive perfluorocompound gases, carrier gases, and the like, the reactor chamber having a reactor effluent gas conduit attached thereto;

b) at least one size selective, preferably glassy polymer, membrane separation unit having a feed side and a permeate side, the membrane being preferentially permeable to at least one carrier gas and being substantially non-permeable to at least one perfluorocompound gas, the membrane unit connected to the reactor chamber via the reactor effluent conduit, the membrane unit further having a permeate vent conduit and a non-permeate conduit, the latter adapted to direct at least a portion of a perfluorocompound containing non-permeate stream from the membrane unit to the reactor chamber. Preferred systems in accordance with the invention further provide pretreatment and/or post-treatment means, such as dry or wet, (or both) scrubbers, thermal decomposers, catalytic decomposers, plasma gas decomposers or filters, prior to the reactor effluent stream entering the membrane unit. In another embodiment, a plurality of membrane units may be arranged in series, either with or without provision of sweep gas on the permeate side of one or all membranes.

Further preferred embodiments of systems of the invention included a damper or surge tank in the non-permeate conduit (preferably between the first or plurality of membrane units and purification unit or storage chamber, or recycle to the reactor chamber); and the provision of a compressor, heat exchanger, cryogenic pump or vacuum pump on one or more of the non-permeate, PFC enriched stream(s), preferably allowing the PFC enriched stream(s) to be stored in liquid form for future use. Also preferred are valves which allow the damper or surge tank and the compressor for creating the liquid PFC mixture to be bypassed.

Preferred processes and systems of the invention include operating one or more of the membrane units at a constant concentration set-point for the PFC concentration in the non-permeate stream from each membrane unit. In this preferred system and process, the set-point concentration of the PFC in the non-permeate stream from each succeeding PFC membrane separation unit would be higher than the immediately preceding one. In this embodiment sensors can be inserted into the non-permeate effluent conduit from each membrane unit to continuously or non-continuously analyze for PFC concentration, or, samples may be taken periodically or continuously from the non-permeate effluent from each membrane unit, which may be sent to dedicated analyzers either on-site or off-site. This information is preferably then forwarded to a process controller which may control for example the pressure of the feed to each membrane unit, temperature, flow, and the like. Also, when a sweep gas arrangement is used, the sweep gas may either be controlled via an open loop or a closed loop arrangement.

Another preferred system and process embodiment of the present invention includes the recycle of the permeate stream of either the first or succeeding stages of the membrane units (in this case, the carrier gas and other process gases are recycled). The carrier gases may be recycled directly to the reactor chambers, or may be liquefied for storage or future use. An additional recycle membrane may be provided, functioning to separate carrier gases from process gases.

Other preferred processes, and systems of the invention are those wherein a waste stream from a pretreatment step for the gas mixture emanating from the semiconductor process is used to generate one or more perfluorocompounds or other chemicals, which may then be purified for use in the semiconductor process, or other chemical processes, as more specifically described in assignee's copending application Ser. No. 08/666,694, filed Jun. 14, 1996 which is incorporated herein by reference.

Still other preferred processes and systems in accordance with the invention are those wherein one or more non-permeate streams is post-treated to remove non-perfluorocompounds. Post-treatment methods may include adsorption, cryogenic distillation, extraction, or scrubbing, previously mentioned as suitable for pretreatment of the feed gas to the membrane.

Another aspect of the invention is a method of recovery of a relatively pure PFC stream from a vent stream from one or more gas cabinets, tube trailers, clean rooms, or the like using a membrane unit as described herein.

Further understanding of the processes and systems of the invention will be understood with reference to the brief description of the drawing and detailed description which follows herein.

BRIEF DESCRIPTION OF THE DRAWINGS

FIG. 12 illustrates schematically a prior art gas cabinet;

FIG. 13 illustrates schematically a gas cabinet including a membrane recovery unit; and FIG. 14 illustrates multiple gas cabinets venting into a common membrane recovery unit.

DESCRIPTION OF PREFERRED EMBODIMENTS

Figure 1:
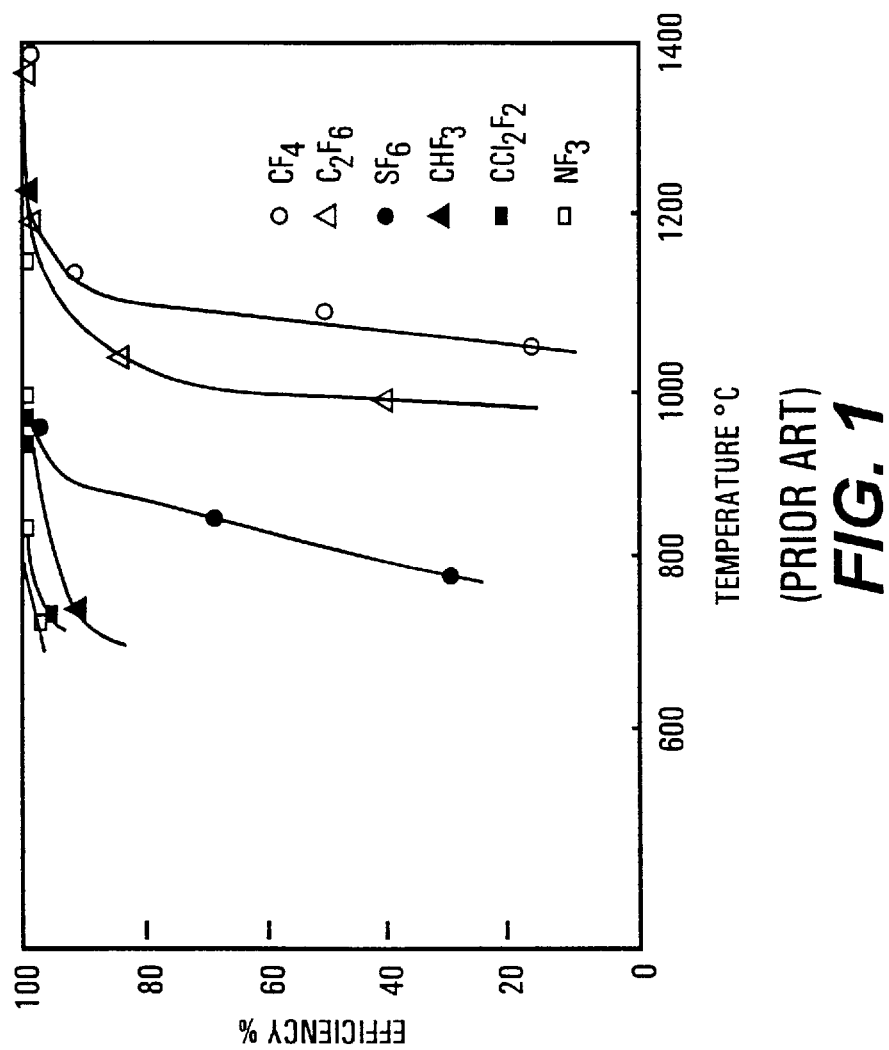
FIG. 1 is a graph illustrating the efficacy of destruction of PFCs with a burner versus the burner flame temperature (prior art)

Recovery of PFCs, for example, from a semiconductor manufacturing process, is now made possible by the present invention using size selective membranes and concentrating a gas mixture comprising PFCs by recovering the non-permeate flow on the non-permeate side of the membrane, while gases non-harmful for the environment permeate through the membrane and can then be directly vented or recycled. This process is simpler and environmentally friendlier than many existing processes. The non-permeate stream may either be rerouted to the semiconductor manufacturing reaction chamber, routed to a storage facility for future use, or routed to a PFC recovery apparatus for separation of PFCs, either on-site or off-site.

Perfluorocompounds, for the purpose of this invention, are defined as compounds comprising C, S and/or N atoms wherein all or all but one hydrogen have been replaced by fluorine. The most common PFCs include, without being limited to, any of the following compounds: fully fluorinated hydrocarbons such as $CF_4$, $C_2F_6$, $C_3F_8$, $C_4F_{10}$, and other fluorinated compounds such as $CHF_3$, $SF_6$, $NF_3$. In defining our invention, PFCs also include $BF_3$, $COF_2$, $F_2$, HF, $SiF_4$, $WF_6$, $WOF_4$, as long as they are not harmful for size selective membranes. Perfluorocompounds do not include chlorofluorocarbons, or compounds comprising two hydrogen substituents or more, and such compounds are not used in semiconductor manufacturing processes.

Size Selective Membranes

In accordance with the present invention, membrane materials suitable for high pressure concentration of PFC's from semiconductor gases exhibit size-selective behavior whereby smaller species such as $N_2$ or He are preferentially permeated versus the larger PFC's. Glassy polymers are one class of polymeric membrane material which largely exhibit this characteristic, but suitable membrane materials are not limited to only glassy polymers.

Important factors such as chain rigidity and free volume are conventional measures which can be used as a first-order screening means to identify suitable polymers. However, a complex interaction of these and other membrane factors, as well as the unique physical characteristics of the PFC gases, complicates selecting of a membrane material with appropriate size-selective capability. Suitable materials can be identified in mixed gas, or in many cases even pure gas, flux measurements. In accordance with this invention, the important criterion for suitable materials is a dominant size selective or mobility selective transport mechanism. A suitable polymer in the practice of this invention exhibits:

$$\frac{[D_c]}{[D_p]} > \frac{[S_c]}{[S_p]}$$

The component mobility (D) and solubility factors can be determined as taught by Chern, R. T., W. J. Koros, H. B. Hopfenburg and V. T. Stannett, Chap. 2 in D. R. Lloyd (Ed.) ACS Sym. Ser. 269, "Materials Science Aspects of Synthetic Membranes," ACS, Washington, D.C. (1984), or Koros, W. J., M. R. Coleman and D. R. B. Walker, "Controlled Permeability Polymer Membranes," Annu. Rev. Mater. Sci, 22, 47–89 (1992).

Solubility selectivity for suitable polymers is typically variable only within a small range. For low free volume materials, which do not exhibit a particular physiochemical affinity for PFC's, a reasonable approximation for the solubility ratio is the ratio of component critical temperatures. For $N_2$ versus $C_2F_6$:

$$T_{cN_2}/T_{cC_2F_6} = 125/293 = 0.43$$

As polymer-free volume increases or with greater polymer/$C_2F_6$ affinity, the $N_2/C_2F_6$ solubility ratio declines due to a greater impact on $C_2F_6$ solubility.

In accordance with the invention, all selectivity between a carrier gas (c) and a perfluorocompound (p), which is defined as $[D_c][S_c]/[D_p][S_p]$, is at least 1.0. In the preferred case, a minimum economically acceptable overall selectivity $N_2/C_2F_6 \geq 5$ is needed, and a minimum mobility selectivity is then estimated, $$\frac{[D_{N_2}]}{[D_{C_2F_6}]} > 11.6$$

The overall selectivity for some polymers useful in the invention is quite large, so actual mobility ratio's exceed the minimum value shown (e.g., ~12). For example, test case selectivities on the order of 200 have been observed, so for some materials $D_i/D_j = 450$.

In accordance with the foregoing, membranes most useful in the invention are preferably glassy membranes, such as polymer membranes made preferably from polyimides, polyamides, polyamide-imides, polyesters, polycarbonates, polysulfones, polyethersulfone, polyetherketone, alkyl substituted aromatic polyesters, blends of polyethersulfone, aromatic polyimides, aromatic polyamides, polyamidesimides, fluorinated aromatic polyamide, polyamide and polyamideimides, glassy polymeric membranes such as disclosed in U.S. Ser. No. 08/247,125 filed May 20, 1994 and incorporated herein by reference, cellulose acetates, and blends thereof, copolymers thereof, substituted polymers (e.g. alkyl, aryl) thereof and the like. Also sulfonated polymers as taught by U.S. Pat. No. 5,364,454 are within the scope of membranes useful in carrying out the present invention.

Asymmetric membranes are prepared by the precipitation of polymer solutions in solvent-miscible nonsolvents. Such membranes are typified by a dense separating layer supported on an anisotropic substrate of a graded porosity and are generally prepared in one step. Examples of such membranes and their methods of manufacture are disclosed in U.S. Pat. Nos. 4,113,628; 4,378,324; 4,460,526; 4,474,662; 4,485,056; 4,512,893; 5,085,676; and 4,717,394 all incorporated herein by reference. Particularly preferred membranes are polyimide asymmetric gas separation membranes as disclosed in U.S. Pat. No. 5,085,676.

Some non-polymeric media fit the criteria for size-selection of gaseous and vapor components, and may be utilized in the practice of the present invention. Two such media which have been described for membrane application are carbon sieve and zeolite membranes. Both of these media separate species by a molecular sieving mechanism. Because of the highly discriminate nature of this process, very high selectivities can be achieved even between molecules of very similar size. For instance, a typical upper bound for $O_2/N_2$ selectivity for polymeric media is 8–10 while carbon sieve membranes have exhibited selectivities on the order of 12–14.

The most successful means of producing carbon sieve membranes has been performed by pyrolysis of a polymeric membrane precursor. Means of producing such membranes and characterization for separation of gaseous materials are described in:

A. Soffer, J. Koresh and S. Saggy, U.S. Pat. No. 4,685,940 (1987); H. Yoneyama and Y. Nishihara, U.S. Pat. No. 5,089,135 (1992); C. W. Jones and W. J. Koros, Carbon, Vol. 32, p. 1419 (1994).

Zeolite coated or filled membranes have also been shown to offer benefits for gaseous and vapor components, and are described in:

K. Kusakabe, S. Yoneshige, A. Murata and S. Morooka, J. Membrane Science, Vol. 116, p. 39 (1996); S. Morooka, S. Yan, K. Kusakabe and Y. Akiyama, J. Membrane Sci., Vol. 101, p. 89 (1995); E. R. Geus, H. van Vekkum, W. J. W. Bakker and J. A. Moulijn, Microporous Mater., Vol. 1, p. 131 (1993); and M. G. Suer, N. Bac and L. Yilmaz, J. Membrane Sci., vol. 9, p. 77 (1994).

Such zeolite coated or filled membranes may be useful in the practice of the present invention.

In a pressure driven gas membrane separation process, one side of the gas separation membrane is contacted with a complex multicomponent gas mixture and certain of the gases of the mixture permeate through the membrane faster than the other gases. Gas separation membranes thereby allow some gases to permeate through them while serving as a barrier to other cases in a relative sense. The relative gas permeation rate through the membrane is a property of the membrane material composition and its morphology. It is believed that the intrinsic permeability of a polymer membrane is a combination of gas diffusion through the membrane, controlled in part by the packing and molecular free volume of the material, and gas solubility within the material. Selectivity is the ratio of the relative permeability of two gases being separated by a material. It is also highly desirable to form defect-free dense separating layers in order to retain high gas selectivity.

Composite gas separation membranes typically have a dense separating layer on a preformed microporous substrate. The separating layer and the substrate are usually different in composition. Composite gas separation membranes have evolved to a structure of an ultrathin, dense separating layer supported on an anisotropic, microporous substrate. Composite membrane structures can be prepared by laminating a preformed ultrathin dense separating layer on top of a preformed anisotropic support membrane. Examples of such membranes and their methods of manufacture are disclosed in U.S. Pat. Nos. 4,664,669; 4,689,267; 4,741,829; 2,947,687; 2,953,502; 3,616,607; 4,714,481; 4,602,922; 2,970,106; 2,960,462; 4,713,292; 4,086,310; 4,132,824; 4,192,824; 4,155,793; and 4,156,597, all incorporated herein by reference.

Alternatively, composite gas separation membranes may be prepared by multistep fabrication processes, wherein first an anisotropic, porous substrate is formed, followed by contacting the substrate with a membrane-forming solution. Examples of such methods are described in U.S. Pat. Nos. 4,826,599; 3,648,845; and 3,508,994, all incorporated herein by reference.

U.S. Pat. No. 4,756,932 describes how composite hollow-fiber membranes may also be prepared by co-extrusion of multiple polymer solution layers, followed by precipitation in a solvent-miscible nonsolvent.

According to one embodiment of the present invention, the membrane can be post-treated with, or coated by, or coextruded with, a fluorinated or perfluorinated polymer layer in order to increase its ability to withstand harmful constituents in the gas mixture from which PFCs are to be separated, at low levels or temporary contact with such components.

The hollow-fiber spinning process depends on many variables which may affect the morphology and properties of the hollow-fiber membrane. These variables include the composition of the polymer solution employed to form the fiber, the composition of fluid injected into the bore of the hollow-fiber extrudate during spinning, the temperature of the spinneret, the coagulation medium employed to treat the hollow-fiber extrudate, the temperature of the coagulation medium, the rapidity of coagulation of the polymer, the rate of extrusion of the fiber, takeup speed of the fiber onto the takeup roll, and the like. It may be preferable to modify the membrane morphology to enhance the separation efficiency. One such method is taught by U.S. Pat. No. 5,468,430.

In accordance with the process of the present invention, the gas mixture containing PFCs to be separated usually comprises at least one PFC and at least one carrier gas such as air, nitrogen, argon, helium, or the like and mixtures thereof.

In Table 1 are listed the most usual PFCs and other gases from a semiconductor manufacturing process (not all of those gases are necessarily present—only some of them may be present).

Typical PFCs for semiconductor processes are the following:

for chamber cleaning: carbon tetrafluoride ($CF_4$), hexafluoroethane ($C_2F_6$), nitrogen trifluoride ($NF_3$), perfluoropropane ($C_3F_8$), sulfur hexafluoride ($SF_6$), trifluoromethane ($CHF_3$);

for etching, the same PFCs are usually used but with several other gases such as argon, boron trichloride, chlorine, hydrogen bromide, hydrogen chloride, hydrogen fluoride, phosphine, silane, silicon tetrachloride, and the like.

Some of these gases are sometimes harmful for the membrane (as indicated in Table 1), and it is preferred to remove or destroy them before introduction or possible contact with the membrane. It is preferred to substantially remove the following compounds prior to sending the flow to the membrane: $WF_6$, HF, $F_2$, $NH_3$, $Cl_2$, HBr, HCl, $O_3$, and any silicon hydrides, germanium hydrides, and the like. To do this, various methods can be used such as using scrubber means (dry or wet scrubbers), thermal decomposition, plasma destruction, catalytic removal, and the like, to reach a level preferably below about 1% vol. of said harmful substance as a percentage of total feed to the membrane. However, it is usually preferred to reach a level for each harmful substance lower than 10 ppm, most preferably lower than 1 ppm. Further, it is possible in certain embodiments to treat the separated PFC non-permeate stream using one or more of those methods, referred to herein as post-treatment.

| Symbol | Name | Harmful to membrane |
|---|---|---|
| PFC'S | | |
| $C_2F_6$ | Hexafluoroethane | not harmful |
| $CF_4$ | Tetrafluoromethane | not harmful |

-continued

| Symbol | Name | Harmful to membrane |
|---|---|---|
| CHF$_3$ | Trifluoromethane | not harmful |
| NF$_3$ | Trifluoride | not harmful |
| SF$_6$ | Sulfur hexafluoride | not harmful |
| C$_3$F$_8$ | Perafluoropropane | not harmful |
| COF$_2$ | Carbonyl fluoride | not harmful |
| | Other gases (carrier gases, etc.) | |
| AR | Argon | not harmful |
| AsH$_3$ | Arsine | not harmful |
| BCl$_3$ | Boron trichloride | not harmful |
| BF$_3$ | Boron trifluoride | not harmful |
| CH$_3$OH | Methanol | not harmful |
| Cl2 | Chlorine | harmful above 1% |
| F$_2$ | Fluorine | harmful above 1% |
| H$_2$ | Hydrogen | not harmful |
| HBr | Hydrogen bromide | harmful above 1% |
| HCl | Hydrogen chloride | harmful above 1% |
| HF | Hydrogen fluoride | harmful above 1% |
| He | Helium | not harmful |
| N$_2$ | Nitrogen | not harmful |
| N$_2$O | Nitrous oxide | not harmful |
| NH$_3$ | Ammonia | harmful above 1% |
| NO | Nitric oxide | not harmful |
| 02 | Oxygen | not harmful |
| 03 | Ozone | harmful above 1% |
| Si(OC$_2$H$_5$)$_4$ | Tetraethyl Orthosilicate (TEOS) | not harmful |
| PH$_3$ | Phosphine | not harmful |
| SiF$_4$ | Silicon tetrafluoride | not harmful |
| SiH$_4$ | Silane | harmful above 1% |
| WF$_6$ | Tungsten hexafluoride | harmful above 1% |
| WOF$_4$ | Tungsten tetrafluoride oxide | not harmful |

SiF$_4$, WF$_6$, WOF$_4$, HF, F$_2$ while being perfluorinated compounds are not considered PFCs.

The scrubber means to remove components potentially harmful to the membrane may include a dry scrubber (which usually removes at least F$_2$, HF, HCl, HBr, Cl$_2$, NH$_3$, WF$_6$ and SiH$_4$) a wet scrubber, or a combination. Dry scrubbers are usually resin-type scrubbers, or soda-lime, while some dry scrubbers comprising catalysts like MnO$_2$ can also remove ozone. Also, gaseous hydrides may be removed according to the methods disclosed in U.S. Pat. Nos. 4,743,435, 4,784,837; 4,910,001; 4,996,030; 5,182,088 and 5,378,439 incorporated herein by reference. When different scrubbers are installed in order to remove the various harmful constituents, it is preferred to flow the gas mixture first to the dry scrubber (or scrubbers) and thereafter to the wet scrubber. Filters to remove particles from the stream are usually necessary (removal of particles having a diameter larger than 20 microns) and it is preferred to provide a filter in the system upstream of the membrane having a pore size diameter less than 20 micrometers and more preferably less than 10 micrometers, thereby removing particles and liquid droplets to avoid imparting membrane performance.

A wet scrubber is, for example, disclosed in the brochure entitled "Selecting a CDO™ for your Particular Application" from DELATECH Corporation.

According to a preferred aspect of the invention, there exist some relationship between the pressure drop across the membrane (i.e. $\Delta P$ between the feed and the permeate), the temperature of the feed (i.e. the temperature of the membrane after temperature equilibration between the feed flow and the membrane itself) and the feed flowrate. In accordance with the present invention, for a given constant flowrate of the feed gas on the membrane and temperature of the feed gas, when the pressure differential across the membrane increases, the recovery of PFCs like e.g. C$_2$F$_6$ decreases on the non-permeate or "residue" side of the membrane while the PFC concentration increases on the permeate side of the membrane. Accordingly, it is preferred, according to the invention, to maintain a pressure drop $\Delta P$ across the membrane which is less than about 13,800 kPa (2000 psia), preferably ranging from about 140 to about 1380 kPa (from about 20 psia to about 200 psia) and most preferably from about 345 and to about 1035 kPa (from about 50 and to about 150 psia).

Because the feed gas mixture is often obtained at substantially atmospheric pressure, it is possible to compress this feed to have a desired pressure drop across the membrane (but this is not preferred because usually, many of the species present in the feed may deteriorate the compressor), or alternatively create on the permeate side of the membrane a pressure lower than feed gas pressure (which is preferred because most of the species which may harm the vacuum means are retained on the non-permeate side of the membrane), or a combination. To create this lowered pressure on the permeate side of the membrane, a vacuum pump or any other suction means is employed. Alternatively, if the feed stream to the membrane is to be compressed, compression is preferably carried out after the feed stream has been pretreated using wet or dry scrubbers, filters, catalytic removal, pulsed corona destruction, thermal decomposition, and/or plasma decomposition, as explained in copending application Ser. No. 08/663,884, filed Jun. 14, 1996, incorporated herein by reference. Preferred compressors are sealed and oil-free, such as the compressors known under the trade designation POWEREX, available from the Powerex Harrison Company, of Ohio, U.S.A. Compression ratio (defined as the ratio of pressure at the compressor outlet divided by the pressure at the compressor inlet) of the compressor which feeds the membrane unit (or the first membrane unit of a series of membrane units) preferably ranges from about 2:1 to about 10:1, it being appreciated that supplemental compression may be required at other membrane feed locations in a series of membrane units. It may be necessary to provide heat exchange between the compressed feed stream and a coolant, such as, for example, ambient liquid water or liquid nitrogen, if the temperature and/or pressure of the feed flowing into a particular membrane is to be controlled, or the PFC concentration in the non-permeate stream is controlled at a set-point value, as disclosed herein.

The temperature of the feed flow and/or the membrane also has an influence on the recovery of PFCs on the non-permeate side of the membrane. Usually, when the feed and/or the membrane temperature increases, then for a given flowrate and pressure drop, a greater quantity of the gas mixture will permeate through the membrane.

Preferably, on-line performance measurements are made using at least one NDIR analyzer which has been calibrated for C$_2$F$_6$, or another component of interest. Remote monitoring and control may be incorporated, for better performance, particularly during excursions in flow and concentration of gas mixtures to be separated.

Preferably, the temperature of the feed and/or the membrane varies from about $-10°$ C. to about $100°$ C., preferably from about $10°$ C. to about $80°$ C., and particularly preferably ranging from ambient temperature (usually about $20°$ C. to $25°$ C.) to about $60°$ C.

Another preferred method of operating the membrane separation units of the process and system of the invention is by operating each membrane unit to have a constant, set-point concentration of one or more PFC gases in the non-permeate stream exiting one or more of the membrane units. Among the advantages of operating the process and system of the invention in this manner are that feed pressure fluctuations can be smoothed, and that the life of the membrane can be prolonged significantly. One way of maintaining the set-point concentration of the PFC in the non-permeate stream is to pass a portion of the non-permeate stream, preferably countercurrently, by the external side of the hollow fiber membrane (that is, on the permeate side of the hollow fibers of the membrane unit). This practice is more fully described in U.S. Pat. Nos. 5,240,471 and 5,383,957, both assigned to L'Air Liquide S.A., with the exception that the patents do not describe separation of PFCs using these techniques. Both of these patents are incorporated herein by reference for their teaching of sweep gas techniques. Thus, a portion or all of a non-permeate stream of a first membrane stage N can be used as feed stream for stage N+1 and/or N+2, etc., bearing in mind that there is usually, in practice, a small pressure drop between stage N, stage N+1 and stage N+2, etc. This means that the pressure on the non-permeate (feed side) of stage N is greater than the pressure on the feed side of any subsequent stage, such as N+1 or stage N+2.

After this first concentration step in embodiments comprising one or a plurality of membranes, it is preferred to then carry out a second step wherein the various PFCs are at least partially separated from each other, or more abundant PFCs separated from minor amounts of other PFCS. Different separation techniques for separating two or more perfluorocompounds can be used such as distillation, adsorption, condensation, and the like. Preferably, and because it may be more appropriate for the streams which are coming out of a semiconductor manufacturing tool, a condensation process can be used such as the one known under the tradename SOLVAL of Air Liquide America Corporation disclosed in the Technical Bulletin entitled "Solval™ Solvent Condensation and Recovery System", 1994, and incorporated herein by reference. Basically, in this condensation process, the effluent from the non-permeate side of one or a plurality of membranes is fed into a heat exchanger. Liquid nitrogen, argon or another cooling medium is introduced into the heat exchanger and flows through the cooling coils. The mixture of PFC with $N_2$ is introduced into the shell of the heat exchanger and flows around the coils as it passes through the shell. The mixture is cooled and part of the PFC vapors are coalesced, liquefied and collected based upon the temperature at the cooling coils. The higher the liquid nitrogen flowrate into the exchanger, the lower the temperature at the cooling coils, and therefore, more of PFCs will be liquefied.

In some preferred embodiments, the PFC mixture after concentration comprises species whose boiling points are close and it is therefore difficult to separate them by fractional condensation. For example, $C_2F_6$ has a normal boiling point of $-78.2°$ C., and $CHF_3$ has a normal boiling point of $-82.1°$ C.; $CF_4$ has a normal boiling point of $-127.9°$ C. and $NF_3$ has a normal boiling point of $-129°$ C. When it is desired to separate a mixture comprising at least two species having close boiling points, then a first separation by, for example, condensation is made between the various species having boiling points not too close from each other in order to provide substantially pure species or a mixture of species having close boiling points. Then, the mixture of species having close boiling points are separated by another process, for example, adsorption when one of the species of the mixture is more polar than the other. $NF_3$ and $CF_4$ may be separated using molecular sieves (such as NaX, CaX, and NaA, or the like); activated carbon; or the like, wherein the polar species (such as $NF_3$ and $CHF_3$) are preferentially adsorbed, as opposed to non-polar species such as $CF_4$.

FIG. 1 illustrates the efficacy of a burner to destroy PFCs versus temperature (°C.) in a prior art process. For example, when an air-fuel burner is used, the temperature of the flame which is reached, if almost 100% of $NF_3$, $CCl_2F_2$ (which is not a PFC but is a chlorofluorocompound used by the electronic industry), $CHF_3$, and $SF_6$ are destroyed (generating HF and other undesirable species), $C_2F_6$ and $CF_4$ are only partially destroyed, particularly $C_2F_6$ which is only 50% destroyed: the combustion gases cannot accordingly be vented. However, when using an oxy-fuel flame which temperature is about 1400° C., it is possible to destroy most of the $C_2F_6$, while still generating undesirable species. In the present invention, combustion at 900° C. may remove all PFCs but $C_2F_6$ and $CF_4$, which may then be separated and optionally recycled.

Figure 2:
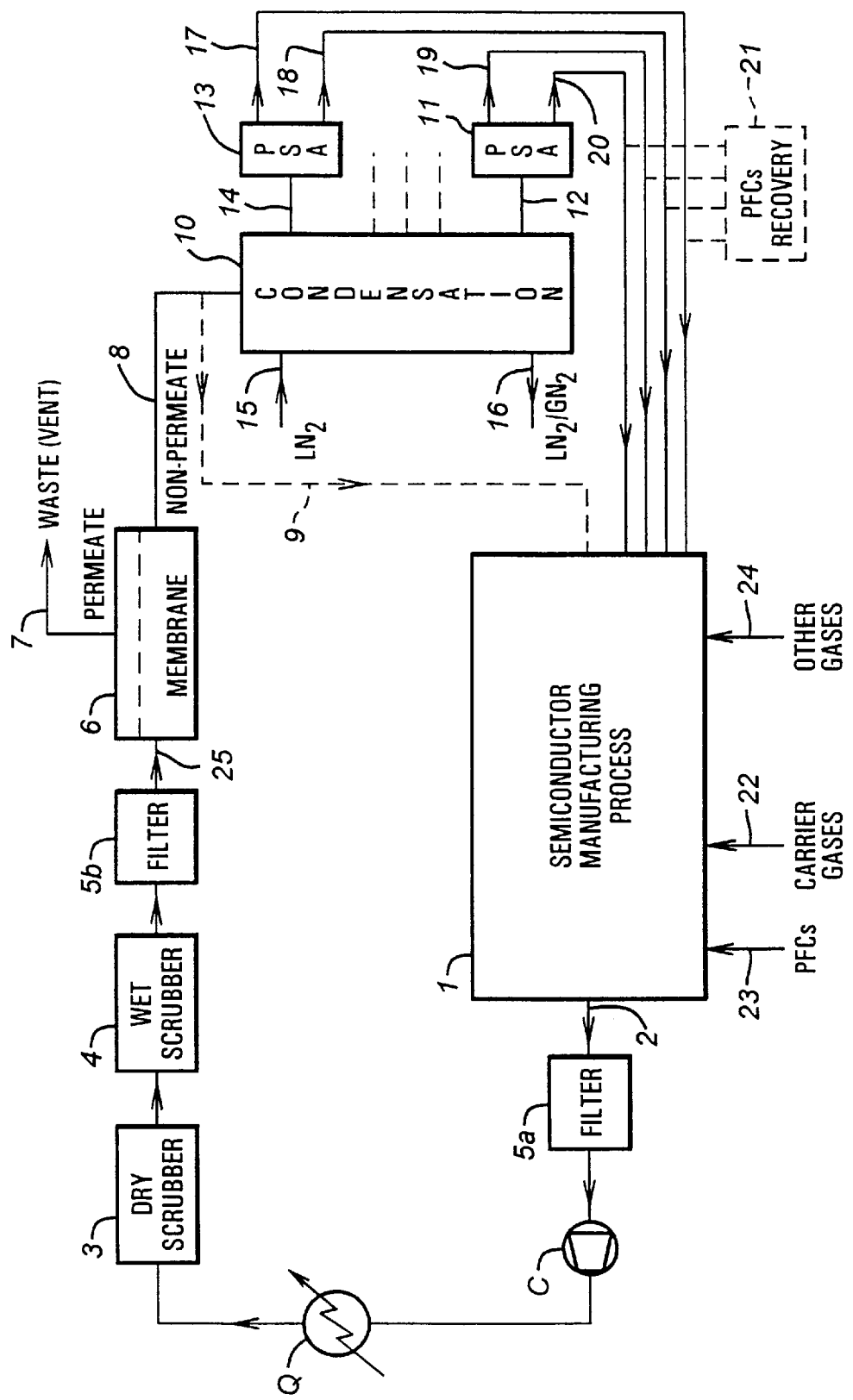
FIG. 2 represents a schematic drawing of one process and system according to the invention.

The general features of one embodiment according to the invention are illustrated in FIG. 2, in a semiconductor manufacturing process 1 (which semiconductor process may be any type of process using PFCs and rejecting PFCs). The PFCs and carrier gases utilized in process 1 are represented by 23 and 22, respectively (typically bulk and/or cylinder delivery through traditional bulk systems or gas cabinets well known in the electronic industry).

In this embodiment, waste gas mixture of PFCs, carrier gases and any other gases 24 (such as chemically reactive gases) is recovered from process 1 in exhaust line 2. The gas mixture is preferably passed through filter 5a, and then compressed in a compressor C. The compressed gas mixture is then optionally routed to a cooler or heater Q to provide a desired temperature for the compressed gas mixture. The gas mixture is then preferably scrubbed in dry scrubber 3 to remove most of silicon hydrides, $NH_3$, $AsH_3$, tetraethyl orthosilicate (TEOS), halogen, halides, then preferably scrubbed in wet scrubber 4 to remove most of hydrides, halides, halogen gases (depending upon the nature of the gas mixture provided in 2, only dry scrubber 3 or wet scrubber 4 may be necessary), then filtered in a filter 5b to remove dust, particles, droplets, and the like, having size greater than 20 micrometers. Additionally, particles and dust may be removed in a filter upstream from dry scrubber 3. A gas mixture in 25 no longer contains any substantial amount of harmful component for membrane unit 6. Gas stream 25 is sent on the feed side of a plurality of hollow fibers of membrane unit 6, the carrier gases of the mixture then permeate through the hollow fibers of membrane unit 6 and are recovered or vented as a waste gas 7 (if, for example, the carrier gas comprises helium, and also argon, it may be useful to recover it and recycle it in the process, with further purification or not). The non-permeate stream which comprises the majority PFCs (concentrated) are recovered in 8 and either directly recycled to process 1 (or stored in bulk to be later reused in process 1) through a line 9 or sent to a separation unit, for example a condensation unit 10. In condensation unit 10, a heat exchanger receives liquid nitrogen $LN_2$ in line 15, which is warmed and leaves unit 10 via line 16 as $LN_2/GN_2$. Unit 10 condenses the high boiling point species (by using different flowrates of $LN_2$, the condensation of various products is controlled) which are recovered as a liquid on line 12 and sent to, for example, a pressure swing adsorption (PSA) process unit 11 which separates the polar fraction from the non-polar fraction (respectively 19, 20), which fractions are either recovered in 21 for further treatment on-site or off-site (the dotted lines indicate that this is not the preferred alternative) or recycled/stored in process 1.

The gaseous fraction from condenser 10 is sent through line 14, to for example a second pressure swing adsorption system 13 (or any other adsorption system) wherein the adsorbed species (one or several) are recovered in line 17 and wherein the non-adsorbed species (one or several) are recovered in line 18. Both products in lines 17 and 18 are either recovered in 21 (for example off-site treatment) or recycled to process 1.

Those species or mixture of species are either recycled to process 1 or recovered in PFC recovery unit 21. At 24 are the other gas inlets in the process (for example chemical gases other than PFCs and other than carrier gases used to dilute the other gases or to purge a chamber). Those other gases are sometimes those which are harmful for the membrane (for example $SiH_4$, $WF_6$, and the like) and which are used in other steps of the manufacturing process of a semiconductor.

Figure 3:
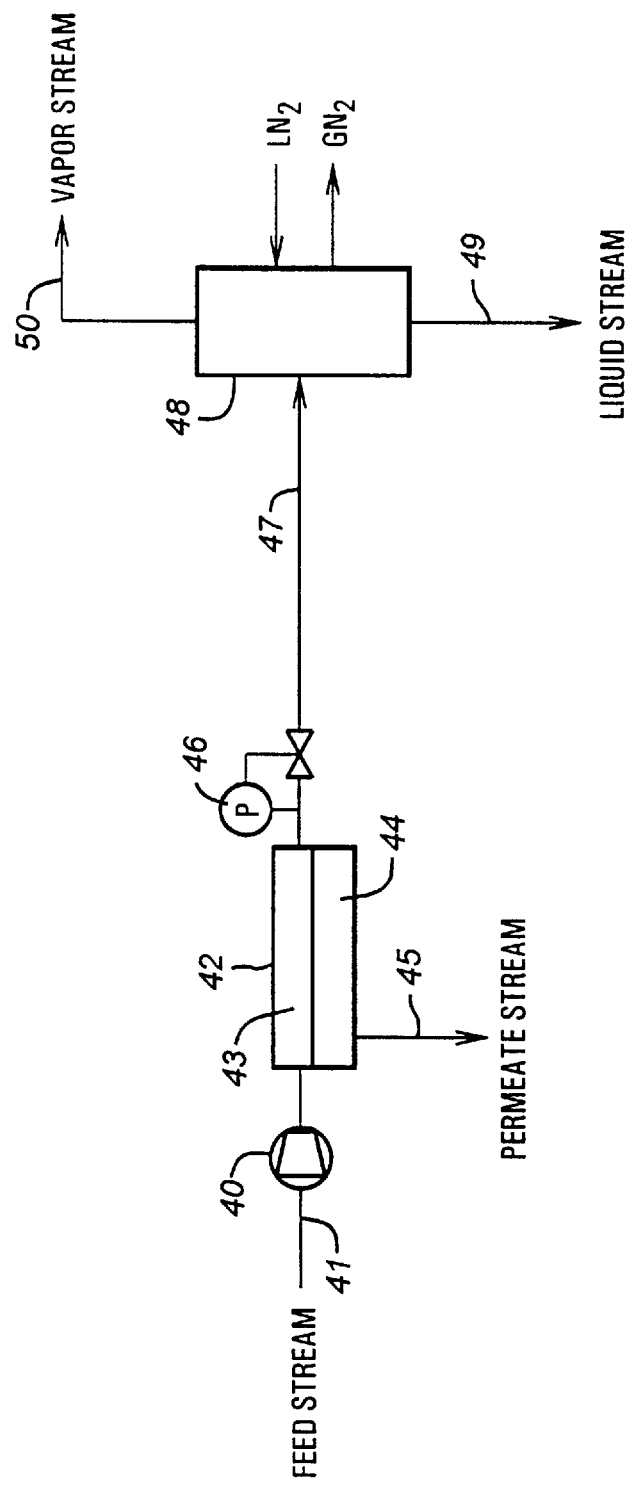
FIG. 3 is a detailed view of a portion of the process and system of FIG. 2.

FIG. 3 is a detailed partial view of FIG. 2 of a preferred membrane system and the condensation system. A feed stream 41 (wherein harmful components have been removed) is compressed in compressor 40 and the stream is fed to the feed side 43 of membrane 42. A permeate stream 45 from the permeate side 44 of the membrane is usually vented. A pressure regulator 46 which may or may not be required controls the pressure downstream of the membrane (on the non-permeate stream), while non-permeate stream 47 is fed, for example, to a condensation system 48, wherein it is separated by heat exchange with liquid nitrogen $LN_2$ to result in condensed stream or liquid stream 49, and uncondensed stream or gaseous stream 50. After heat exchange, the liquid nitrogen $LN_2$ is substantially totally vaporized as gaseous nitrogen $GN_2$.

Figure 4:
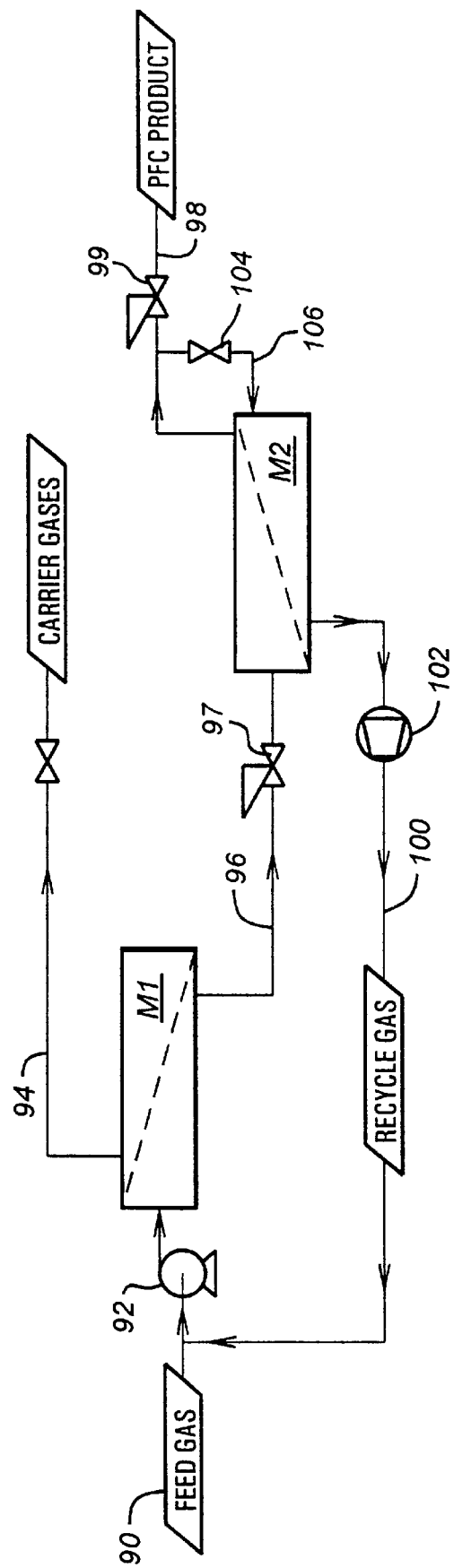
FIGS. 4, 4a, 5, 6 and 7 illustrate different embodiments of the invention.

FIG. 4 represents a simplified schematic diagram of one process and system embodiment of the present invention. Feed gas 90 from a semiconductor manufacturing process is compressed in compressor 92 prior to entering a first stage membrane M1. First stage (N) membrane M1 creates a permeate stream 94 comprised primarily of carrier and process gases, and a non-permeate stream 96, enriched in one or more PFCs. A back pressure regulator 97 provides a pressure drop across membrane M1. Non-permeate stream 96 then enters a second stage (N+1) membrane M2, producing a second non-permeate PFC enriched stream 98, and a second stage permeate stream 100 comprised primarily of carrier and process gases which are impermeable to the M1 membrane but which are permeable to the M2 membrane. A second back pressure regulator 99 maintains a pressure drop across second stage membrane M2. Optionally, streams 94 and 100 may be combined and either disposed of, or recycled as shown for stream 100. Optional and preferred components of the system embodied in FIG. 4 include provision of a valve 104 and conduit 106 which allow a portion of the PFC product stream 98 to be swept across the permeate side of membrane M2, thereby affording process efficiencies as described in the '471 and '957 patents, previously incorporated by reference. Also, an optional vacuum means 102 is illustrated on the recycled gas stream. Vacuum pump 102, if present, allows recycled gas stream 100 to reenter the system with the feed gas. Optionally, where vacuum means 102 is provided, it may be utilized with or without the pressure of compressor 92.

Figure 4A:
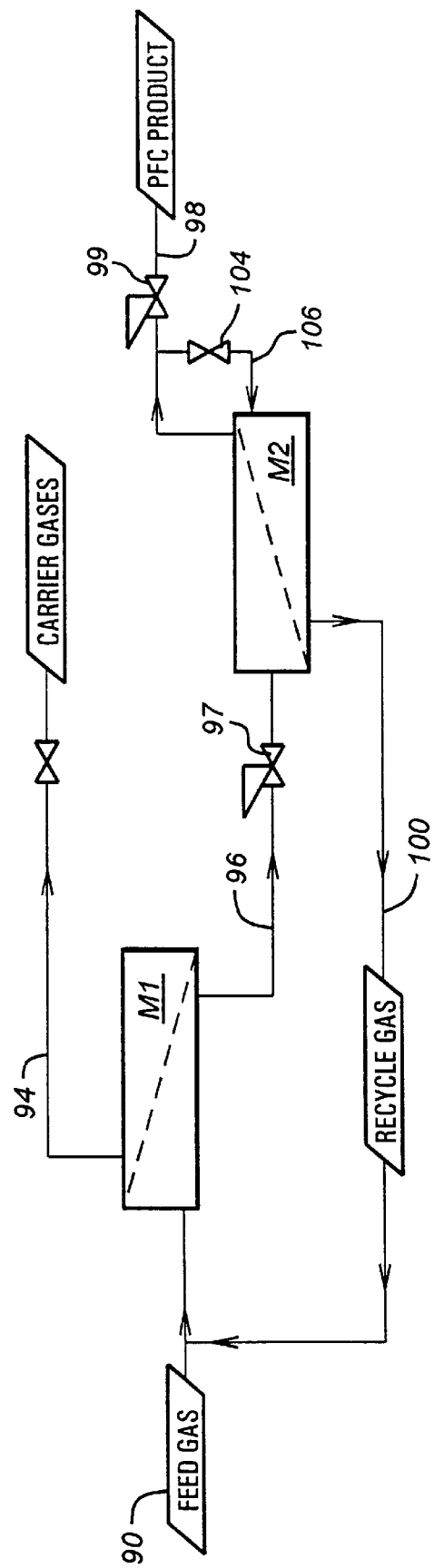

FIG. 4a represents the embodiment of FIG. 4, where the vacuum and compressor means are not installed.

Figure 5:
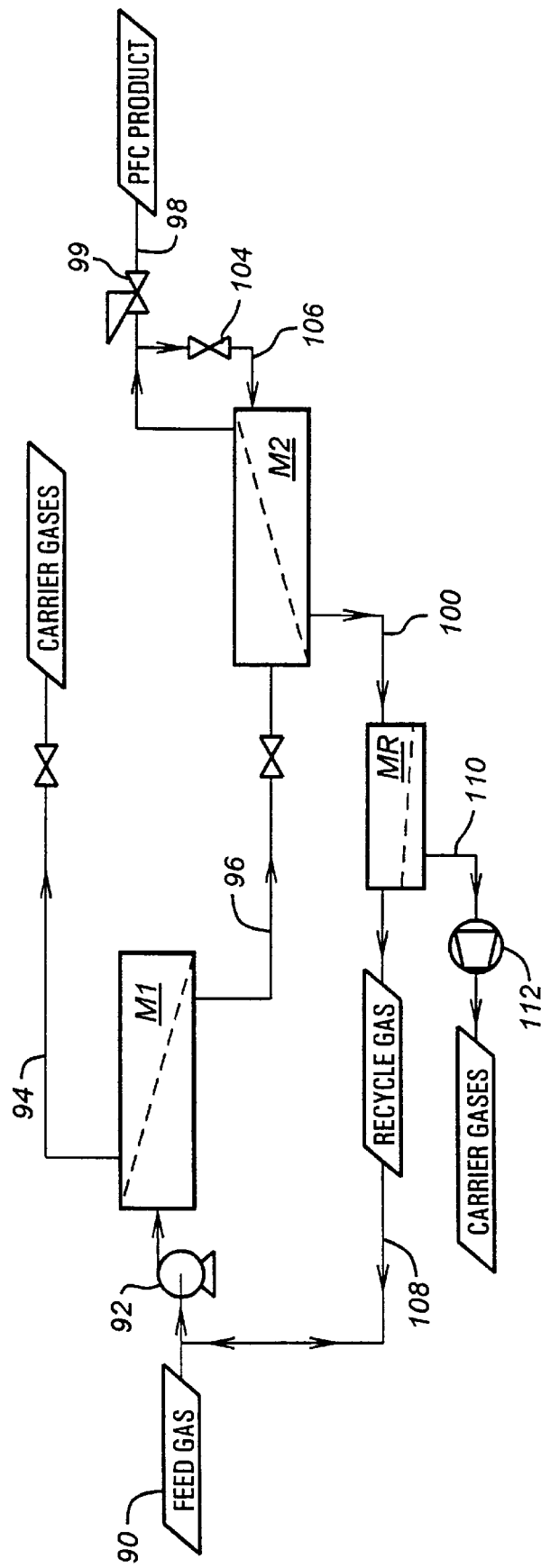

FIG. 5 illustrates a system and process substantially in accordance with that of FIG. 4, with the provision of a recycle membrane $M_R$ in recycle gas line 100. Also optionally provided is a conduit 110 and vacuum pump 112 which allows separation via recycle membrane MR of carrier gases. The recycle gases in conduit 108 are comprised primarily of other process gases as defined herein.

Figure 6:
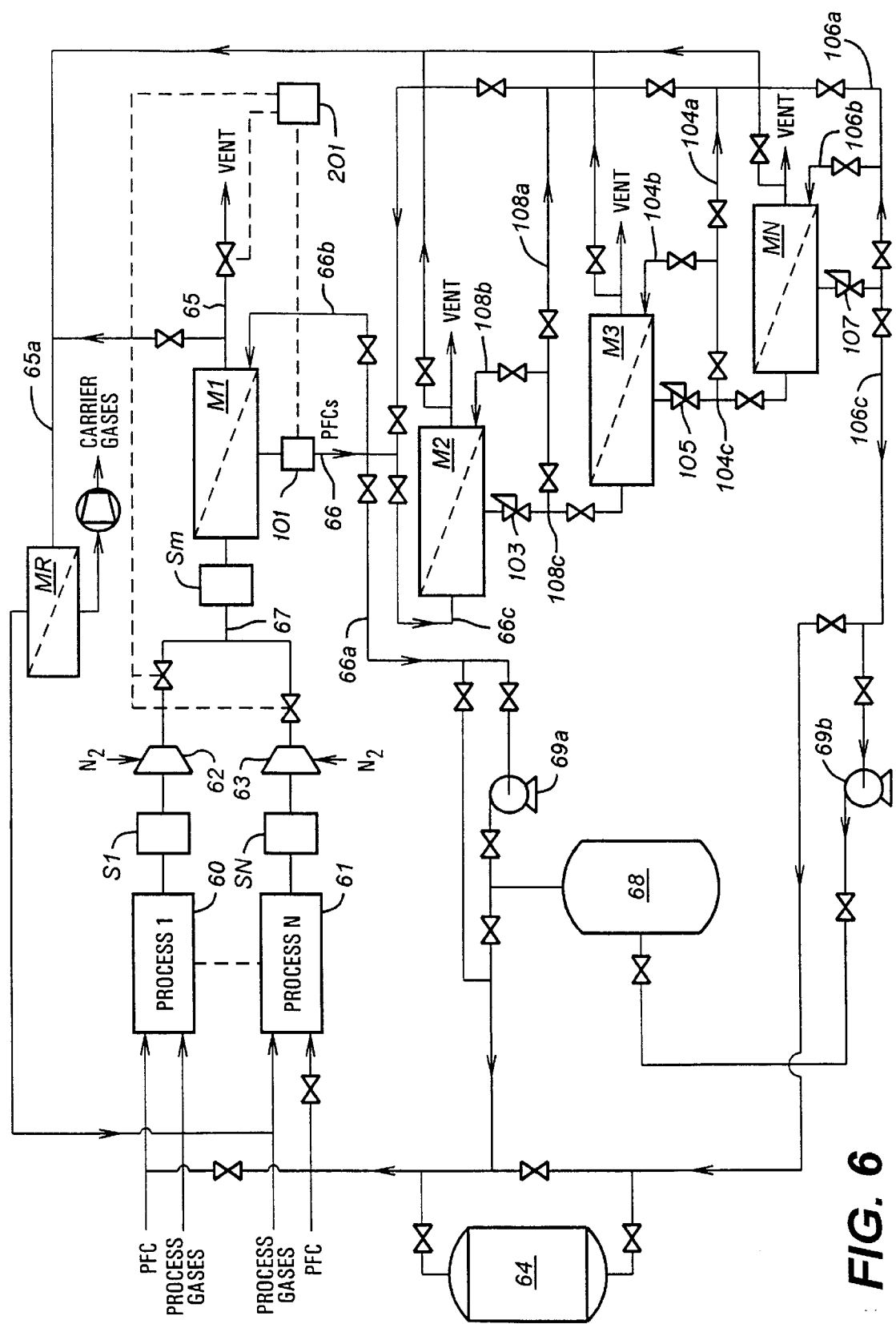
Figure 7:
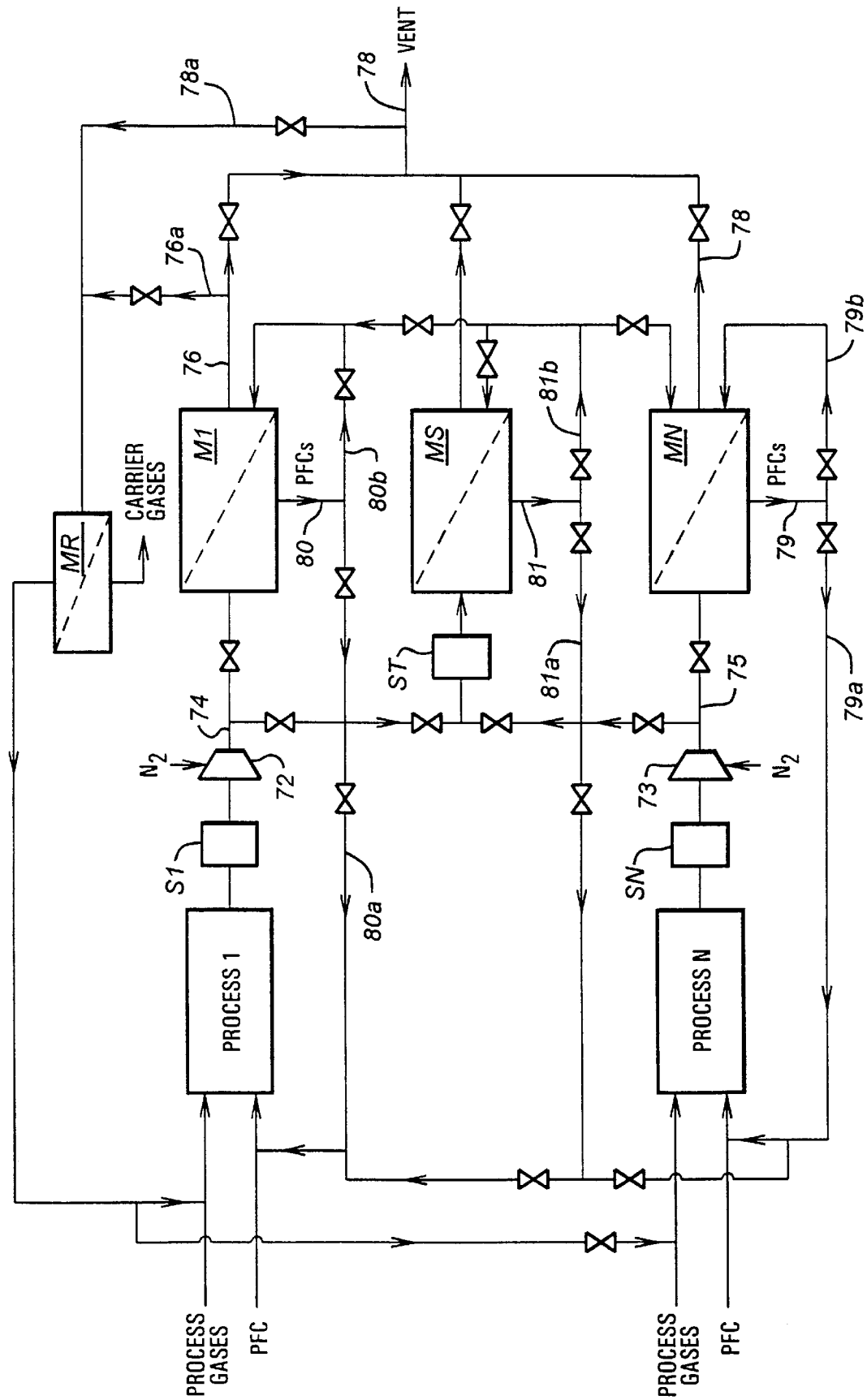

FIGS. 6 and 7 illustrate two other possible embodiments of the invention. In FIG. 6, several identical or different processes 60 . . . 61 are present (either simultaneously or not), using similar or different PFC gases and other gases designated as process gases. The gas exhausts from 60 . . . 61 are preferably scrubbed in scrubbers $S_1$, $S_N$, and then are preferably diluted with $N_2$, and compressed respectively in 62 . . . 63, and mixed together as a single stream 67 (in fact the various processes 1 . . . N may either successively or simultaneously discharge exhaust gases). Single stream 67 is then preferably filtered at $S_m$ as a final cleaning step, then fed to a membrane unit M1 of the invention wherein the permeate 65 may be vented and a non-permeate 66 and 66a (concentrated PFCs) may be recycled to one or several of the processes 1 . . . N, respectively 60 . . . 61. Alternatively, non-permeate stream 66c may be routed to one or more membrane units $M_2$, $M_3$, . . . $M_N$, thus improving the purity of the PFCs. Preferably, a sweep gas stream 66b may be employed to sweep the permeate side of M1. Membrane units $M_2$, $M_3$ and $M_N$ also may have sweep gas streams. Other preferred features of this embodiment of the invention include the provision of one or more vacuum pumps (69a and 69b), a high pressure PFC storage vessel 68, and/or a surge tank 64. As an example of multiple different processes, one process may be a metal oxide etch, another might be an oxide etch, and yet another might be a tungsten CVD process. A recycle membrane MR may be included in preferred systems, wherein all or a portion 65a of permeate stream 65 may be fed to separate process gases from carrier gases.

Further illustrated in FIG. 6 is a mass flow measurement device 101 on the non-permeate stream 66 of membrane unit $M_1$ which may be used to control the flow of the permeate stream indirectly via controller 201, which in this case accepts a signal from flow measurement device 101 and adjusts flow control valves in conduits 67 and 65. Conduit 66 also preferably includes a backpressure regulator, which is not illustrated for clarity. Backpressure regulators 103, 105, and 107 serve the function as described above for backpressure regulator 97 depicted in FIG. 4. For example, it may be advantageous, as previously mentioned, to operate M1 using a set point PFC concentration in the non-permeate stream 66. In such embodiments, the flow measurement device may also include analysis equipment to determine the PFC concentration in conduit 66. Similar process controls may be used for membrane units M1, M2, M3, and MN as desired. Also, similar piping arrangements may be employed in the down stream membrane units, as denoted at 108a, 108b, 108c, 104a, 104b, 104c, 106a, 106b, and 106c.

FIG. 7 is a parallel processing embodiment wherein each process 1 . . . N is associated (after dilution with nitrogen and compression respectively in 72 and 73) with a membrane system $M_1$ . . . $M_N$, respectively, according to the invention. Each feed stream 74 . . . 75 is fed to a membrane system $M_1$ . . . $M_N$ (with pretreatment systems $S_1$ . . . $S_N$ if necessary). The permeate gases (76, 78) are vented together at 78 or recycled via lines 76a and 78a to recycle membrane MR, while each non-permeate 79, 80, 81 is recycled, preferably to its corresponding process lines 79a, 80a, and 81a, respectively. Preferred features of this embodiment include a redundant membrane unit $M_S$, preferably having its own pretreatment unit $S_T$. Also preferred is a recycle membrane unit $M_R$, which separates usable reactive process gases from carrier gases. With suitable arrangement of valves, this embodiment can operate in parallel or series (cascade) mode. As described previously in reference to FIG. 4, a portion of each non-permeate stream may be used as a sweep of the permeate side of its respective membrane, via lines 79b, 80b, and 81b.

For all different embodiments of the invention, it is preferred to create a pressure drop across the membrane. In one embodiment this may be done by creating vacuum on the permeate side of the membrane while keeping the feed gas at about atmospheric pressure, which is usually about the pressure of the gas mixture released from the semiconductor manufacturing process. Because usually only the carrier gases permeate through the membrane, damage to a vacuum pump or other vacuum system is minimized, while on the contrary, compressing the gas mixture upstream from the membrane would not only mean compressing more gas, but it would also mean a risk for the compressor means.

Figure 8:
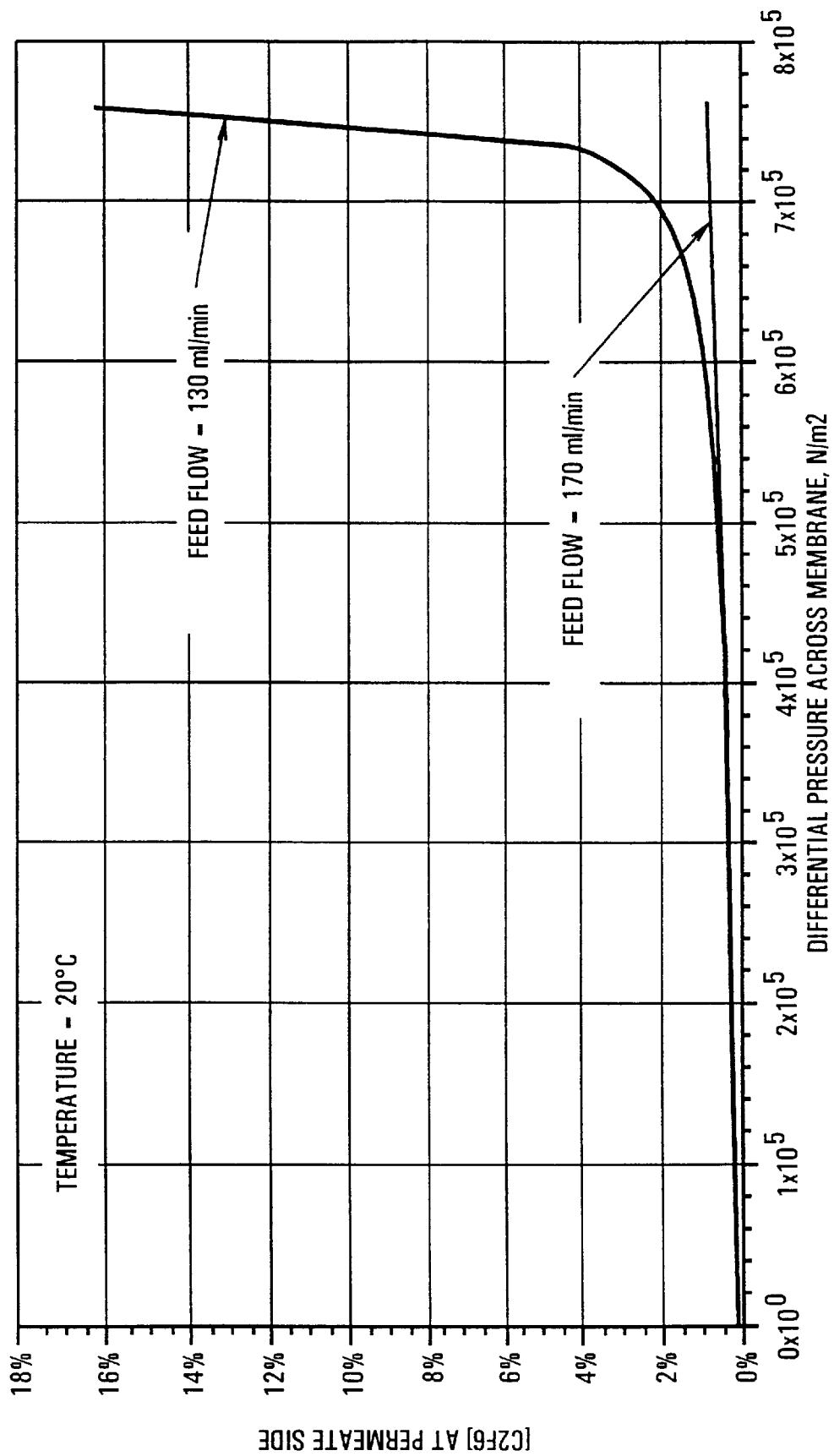
FIG. 8 illustrates PFC concentration on the permeate side of the membrane versus the pressure differential across the membrane, for different flowrates of the feed stream.

FIG. 8 illustrates at 20° C., two different flowrates of the feed flow of 170 ml/min and 130 ml/min, respectively, on a hollow-fiber membrane made of glassy polymer having a surface of about 0.2 $m_2$ wherein the feed flow is sent into the hollow fiber with a permeation towards the outside hollow fiber. FIG. 8 clearly illustrates for low pressure drop between the non-permeate and the permeate sides of the membrane, almost no concentration of $C_2F_6$ occurs (0.2% of $C_2F_6$ recovered on the non-permeate side with the "residue"). For higher pressure drops, depending on the feed flow, the concentration of $C_2F_6$ then increases with an onset point of about $7 \times 10^5$ $N/m^2$ ($\Delta P$ across the membrane) for a feed flow of 130 ml/min. For higher flowrates (170 ml/min.) the onset point is obviously higher (increases with feed flow).

Figure 9:
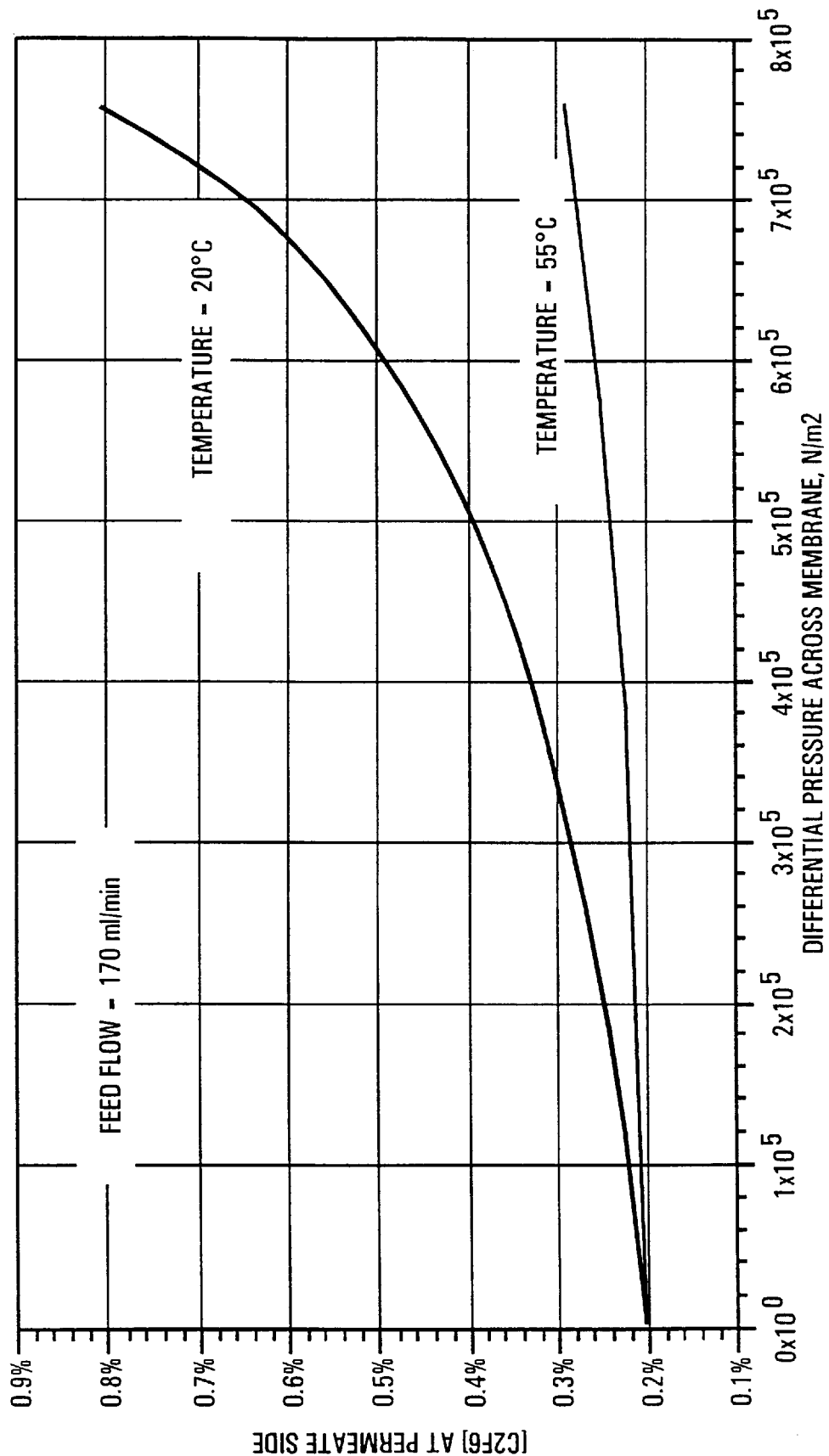
FIG. 9 illustrates PFC concentration on the permeate side of the membrane versus the pressure differential across the membrane, for different temperatures of the feed flow.

FIG. 9 illustrates the effect of the temperature of the feed flow (or of the membrane) utilizing the same type membrane as used for FIG. 8. For a higher temperature of the flow, a higher differential pressure across the membrane is needed to achieve the same concentration of PFCs.

Figure 10:
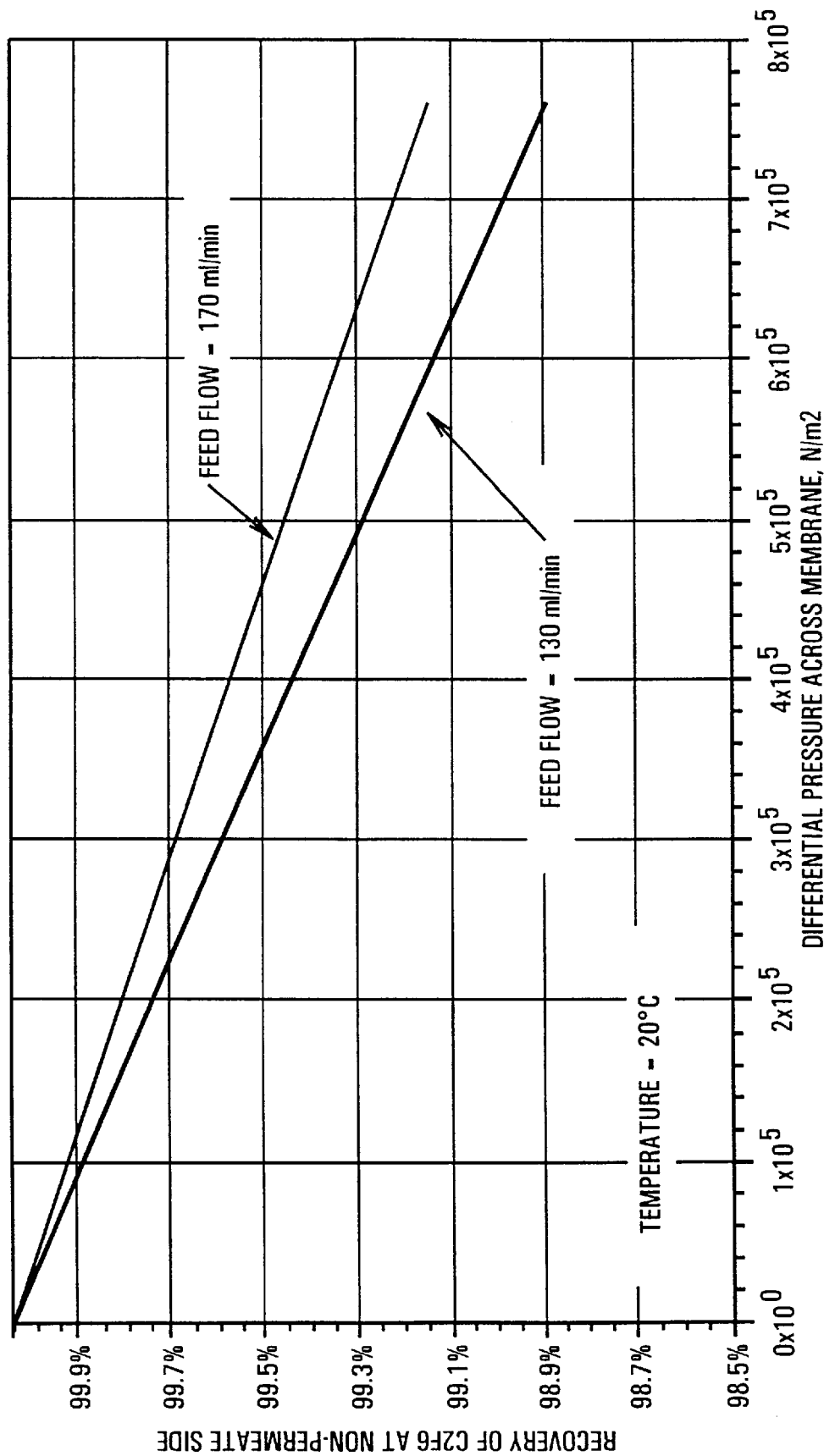
FIG. 10 illustrates PFC concentration on the recovery side (non-permeate side) of the membrane versus the pressure differential across the membrane, for different flowrates of the feed stream.

FIG. 10 illustrates the recovery rate of $C_2F_6$, on the non-permeate side of the membrane versus the differential pressure across the membrane for two different flowrates: for very low differential pressure, about all of the $C_2F_6$ is recovered while the rate of $C_2F_6$ permeating through the membrane progressively increases with the pressure drop across the membrane, such rate increasing faster for lower flowrates (compare curves for 130 ml/min. and 170 ml/min).

Figure 11:
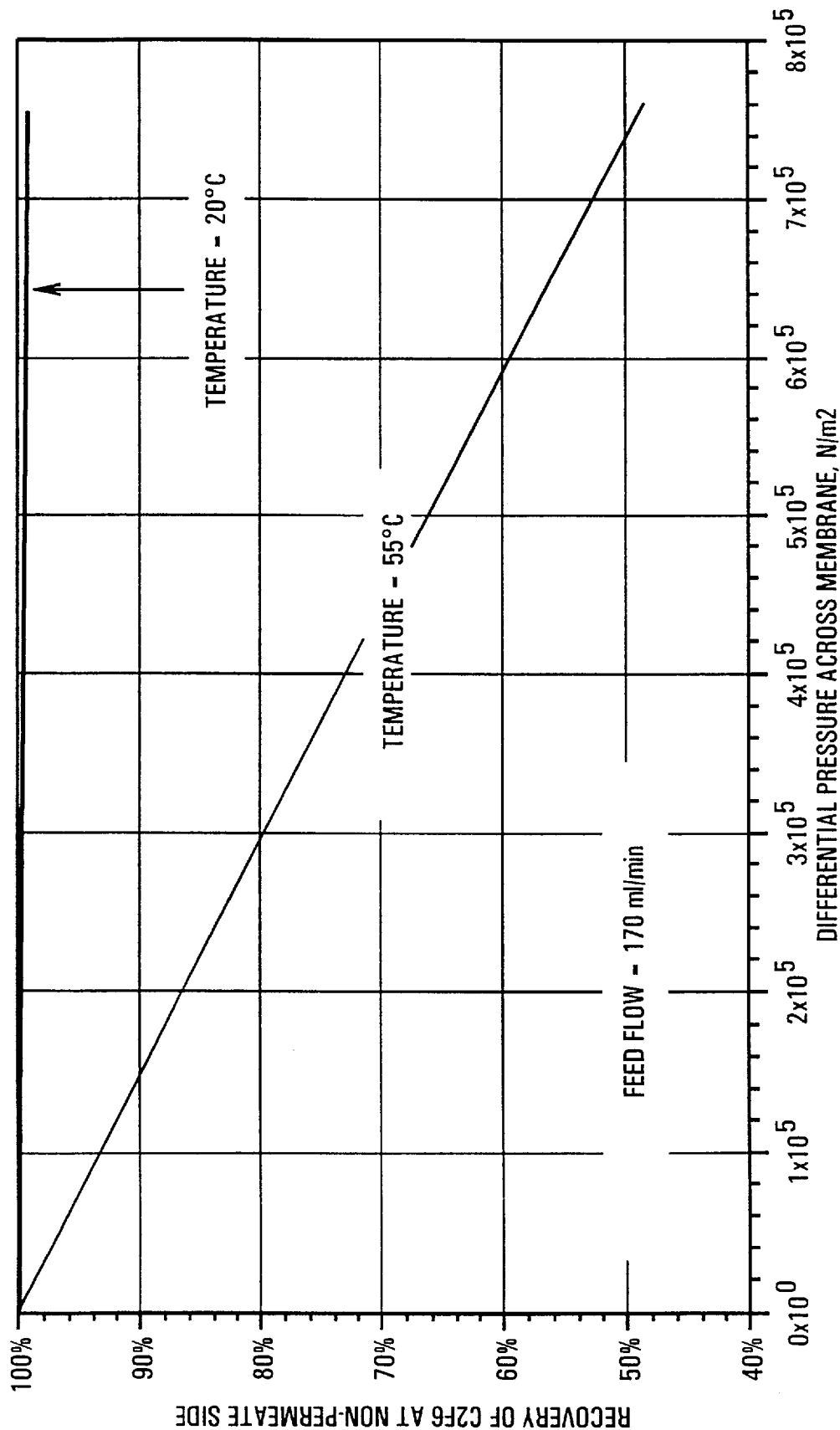
FIG. 11 illustrates PFC concentration on the recovery side (non-permeate side) of the membrane versus the pressure differential across the membrane, for different temperatures of the feed flow.

FIG. 11 illustrates the effect of temperature for a flow of 170 ml/min. While only an extremely low amount of $C_2F_6$ permeates at 20° C., almost half of it permeates at 55° C. for a pressure drop of about $7 \times 10^5$ $N/M^2$.

From a recovery standpoint, FIGS. 10 and 11 show it is thus better to operate at high flowrates and ambient temperature for a given pressure drop. But FIGS. 8 and 9 indicate that a substantial pressure drop is necessary to have a certain purity of $C_2F_6$ (and thus a certain concentration).

FIGS. 12–14 illustrate another aspect of the invention. Gas cabinets (sometimes known as gas panels) are well known in the semiconductor manufacturing art and need little explanation to the skilled artisan. A gas cabinet for PFCs will have a PFC vent stream. PFC vents from tube trailers, clean rooms, gas packaging facilities, and the like, also are well known and need little explanation. Although the following discussion is for gas cabinet vents, the idea pertains to the recovery of a relatively pure PFC stream from any venting of PFCs. Automated cabinets employ specific purging routines before and after cylinder change. Pre-purge routine generally is utilized to purge process gas while a post-purge routine is generally used to remove purging intrusions.

FIG. 13 illustrates schematically the provision of a pure PFC stream to a gas cabinet 150 (the internals are not illustrated for clarity). Conduit 120 provides a pure PFC stream to gas cabinet 150. Gas cabinet 150 has a vent tube or conduit 180 which leads to a membrane separator unit 200 having a non-permeate stream 220 and a permeate stream 240 as explained herein.

FIG. 14 illustrates schematically the provision of multiple (in this case three) gas cabinets 150a, 150b, and 150c, all venting into a common membrane recovery unit 200.

EXAMPLES

Example 1

A feed stream comprising 0.95% vol. $C_2F_6$, 1.03% vol. $CHF_3$, 1.10% $CF_4$, and 96.93% nitrogen at a pressure of 544,218 Pascal, a temperature of 293 K (20° C.) and a flowrate of 193 sl/m (standard liter per minute) is fed on the feed side of a polyimide membrane made according to U.S. Pat. No. 5,085,676. A vacuum system creates a low pressure on the other side of the membrane: the permeate stream recovered is at a pressure of 6,579 Pascal, a temperature of 293 K and a flowrate of 181 sl/m, while on the non-permeate side, the pressure remains 544,218 Pascal, the temperature 293 K and the flowrate 12 sl/m. The non-permeate (concentrated) stream from the membrane comprises:

| | |
|---|---|
| $C_2F_6$ | 15.66% vol. |
| $CHF_3$ | 9.54% vol. |
| $CF_4$ | 18.15% vol. |
| $N_2$ | 56.65% vol. |

The permeate stream from the membrane comprises:

| | |
|---|---|
| $C_2F_6$ | 0.02% vol. |
| $CHF_3$ | 0.48% vol. |
| $CF_4$ | 0.01% vol. |
| $N_2$ | 99.49% vol. |

The non-permeate stream is further sent to a cryogenic condensation system as disclosed hereabove wherein 0.4942 pound of liquid nitrogen per pound of non-permeate stream is contacted by heat exchange, thus condensing most of the PFCs as indicated hereafter. The compositions of the vapor and liquid streams are the following:

Vapor Stream:

| | |
|---|---|
| $C_2F_6$ | 1.03% vol. |
| $CHF_3$ | 0.69% vol. |
| $CF_4$ | 16.5% vol. |
| $N_2$ | 81.78% vol. |

This vapor stream comprises essentially $CF_4$ diluted in nitrogen.

Liquid Stream

| | |
|---|---|
| $C_2F_6$ | 47.83% vol. |
| $CHF_3$ | 29.00% vol. |
| $CF_4$ | 21.81% vol. |
| $N_2$ | 1.37% vol. |

The liquid stream is essentially concentrated into three liquid species $C_2F_6$, $CHF_3$ and $CF_4$. The liquid stream is then either recycled into the process from where the feed flow was coming or recovered and shipped for further treatment (concentration, separation, etc.).

The vapor stream is preferably recycled to the input of the cryogenic condensation system or may be treated (for example scrubbed) and discarded.

Example 2

Under the same conditions as in Example 1, a feed stream comprising 0.95% vol. $C_2F_6$, 1.03% vol. $CHF_3$, 1.10% $CF_4$, and 96.93% nitrogen at a pressure of 544,000 Pascal, a temperature of 20° C. and a flowrate of 193 sl/m (standard liter per minute) is sent on the same membrane as in Example 1, said membrane being connected to the same cryogenic separation system using liquid nitrogen. The non-permeate (concentrated) stream from the membrane comprises:

| | |
|---|---|
| $C_2F_6$ | 15.66% vol. |
| $CHF_3$ | 9.54% vol. |
| $CF_4$ | 18.15% vol. |
| $N_2$ | 56.65% vol. | at the same temperature and pressure as the feed stream, but at a flowrate of 12 sl/m.

The permeate stream from the membrane comprises:

| | | |
|---|---|---|
| $C_2F_6$ | 0.02% vol. | |
| $CHF_3$ | 0.48% | vol. |
| $CF_4$ | 0.01% | vol. |
| $N_2$ | 99.49% vol. | |

The non-permeate stream is further sent to the cryogenic separation system disclosed in Example 1 and the following vapor and liquid streams are obtained:

Vapor Stream:

| | |
|---|---|
| $C_2F_6$ | 1.03% vol. |
| $CHF_3$ | 0.69% vol. |
| $CF_4$ | 16.5% vol. |
| $N_2$ | 81.78% vol. |

Liquid Stream

| | |
|---|---|
| $C_2F_6$ | 47.83% |
| $CHF_3$ | 29.00% |
| $CF_4$ | 21.81% |
| $N_2$ | 1.37%. |

The liquid stream is essentially concentrated into three liquid species $C_2F_6$, $CHF_3$ and $CF_4$. The liquid and vapor streams are e.g. treated as explained in Example 1.

Example 3

Under the same conditions as in Example 1, a feed stream comprising 0.20% vol. $C_2F_6$, 0.01% vol. $CHF_3$, 0.06% $CF_4$, 0.01% $NF_3$, 0.01% $SF_6$ and 99.71% nitrogen at a pressure of 714,286 Pascal, a temperature of 20° C. and a flowrate of 199 sl/m (standard liter per minute) is sent on the same membrane as in Example 1, said membrane being connected to the same cryogenic separation system using liquid nitrogen. The non-permeate (concentrated) stream from the membrane comprises:

| | |
|---|---|
| $C_2F_6$ | 0.5381% vol. |
| $CHF_3$ | 0.02% vol. |
| $CF_4$ | 0.1611% vol. |
| $NF_3$ | 0.0245% vol. |
| $SF_6$ | 0.0271% vol. |
| $N_2$ | 99.2291% vol. |

(At the same temperature and pressure than the feed stream, but at a flowrate of 73 sl/m.)

The permeate stream from the membrane comprises:

| | |
|---|---|
| $C_2F_6$ | 0.0041% vol. |
| $CHF_3$ | 0.0047% vol. |
| $CF_4$ | 0.0014% vol. |
| $NF_3$ | 0.0016% vol. |
| $SF_6$ | 0.0004% vol. |
| $N_2$ | 99.9878% vol. |

The pressure of the permeate is 6579 Pascal with a flowrate of 126 sl/m. The non-permeate stream is further sent to the cryogenic separation system disclosed in Example 1 (0.4335 pound of $LN_2$ for each pound of non-permeate stream) and the following vapor and liquid streams are obtained:

Vapor Stream:

| | | |
|---|---|---|
| $C_2F_6$ | 0.3418% | Pressure: 714,286 Pascal |
| $CHF_3$ | 0.0125% | Temperature: 144 K. |
| $CF_4$ | 0.1592% | Flowrate: 72.8 sl/m. |
| $NF_3$ | 0.0242% | |
| $SF_6$ | 0.0118% | |
| $N_2$ | 99.4505% | |

Liquid Stream

| | | |
|---|---|---|
| $C_2F_6$ | 85.9100% | Pressure: 714,286 Pascal |
| $CHF_3$ | 3.2800% | Temperature: 144 K. |
| $CF_4$ | 0.9900% | Flowrate: 0.2 sl/m. |
| $NF_3$ | 0.1400% | |
| $SF_6$ | 6.6900% | |
| $N_2$ | 2.9900% | |

Example 4

Under the same conditions as in Example 1, a feed stream comprising 0.20% vol. $C_2F_6$, 0.01% vol. $CHF_3$, 0.06% $CF_4$, 0.01% $NF_3$, 0.01% $SF_6$ and 99.71% nitrogen at a pressure of 319,728 Pascal, a temperature of 20° C. and a flowrate of 170 sl/m (standard liter per minute) is sent on the same membrane as in Example 1, said membrane being connected to the same cryogenic separation system using liquid nitrogen. The non-permeate (concentrated) stream from the membrane comprises:

| | |
|---|---|
| $C_2F_6$ | 0.5600% vol. |
| $CHF_3$ | 0.0200% vol. |
| $CF_4$ | 0.1700% vol. |
| $NF_3$ | 0.0300% vol. |
| $SF_6$ | 0.0300% vol. |
| $N_2$ | 99.2000% vol. |

(At the same temperature and pressure than the feed stream, but at a flowrate of 112 sl/m.)

The permeate stream from the membrane comprises:

| | |
|---|---|
| $C_2F_6$ | 0.0154% vol. |
| $CHF_3$ | 0.0041% vol. |
| $CF_4$ | 0.0039% vol. |
| $NF_3$ | 0.0019% vol. |
| $SF_6$ | 0.0009% vol. |
| $N_2$ | 99.9738% vol. |

The pressure of the permeate is 6579 Pascal with a flowrate of 112 sl/m. The non-permeate stream is further sent to the cryogenic separation system disclosed in Example 1 (0.4335 lb. of $LN_2$ for each lb. of non-permeate stream) and the following vapor and liquid streams are obtained:

Vapor Stream:

| | | |
|---|---|---|
| $C_2F_6$ | 0.0072% | Pressure: 714,286 Pascal |
| $CHF_3$ | 0.0003% | Temperature: 144 K. |
| $CF_4$ | 0.1145% | Flowrate: 72.8 sl/rn. |
| $NF_3$ | 0.0197% | |
| $SF_6$ | 0.0003% | |
| $N_2$ | 99.8580% | |

Liquid Stream

| | | |
|---|---|---|
| $C_2F_6$ | 80.67% | Pressure: 714,286 Pascal |
| $CHF_3$ | 2.88% | Temperature: 144 K. |
| $CF_4$ | 8.21% | Flowrate: 0.2 sl/m. |
| $NF_3$ | 1.52% | |
| $SF_6$ | 4.34% | |
| $N_2$ | 2.38% | |

Example 5

Under the same conditions as in Example 2, a feed stream comprising 1.00% vol. $C_2F_6$, 0.01% vol. $CHF_3$, 0.01% $CF_4$, and 98.96% nitrogen at a pressure of 866,595 Pascal, a temperature of 20° C. and a flowrate of 5,000 sl/m (standard liter per minute) is sent on the same membrane (first membrane) as in Example 1, said membrane being connected to a second membrane (cascade connection: non-permeate side of the first to the feed side of the second). The non-permeate (concentrated) stream from the first membrane comprises:

| | |
|---|---|
| $C_2F_6$ | 33.93% vol. |
| $CHF_3$ | 0.17% vol. |
| $CF_4$ | 0.31% vol. |
| $NF_3$ | 0.17% vol. |
| $SF_6$ | 0.31% vol. |
| $N_2$ | 65.11% vol. |

At the same temperature and pressure than the feed stream, but at a flowrate of 150 sl/m.

The permeate stream from the first membrane comprises:

| | |
|---|---|
| $C_2F_6$ | 0.0012% vol. |
| $CHF_3$ | 0.0053% vol. |
| $CF_4$ | 0.0009% vol. |
| $NF_3$ | 0.0052% vol. |
| $SF_6$ | 0.0009% vol. |
| $N_2$ | 99.9865% vol. |

The non-permeate (concentrated) stream from the second membrane comprises:

| | |
|---|---|
| $C_2F_6$ | 96.52% vol. |
| $CHF_3$ | 0.23% vol. |
| $CF_4$ | 0.81% vol. |
| $NF_3$ | 0.24% vol. |
| $SF_6$ | 0.81% vol. |
| $N_2$ | 0.39% vol. |

The permeate stream from the second membrane comprises:

| | |
|---|---|
| $C_2F_6$ | 0.0636% vol. |
| $CHF_3$ | 0.1358% vol. |
| $CF_4$ | 0.0424% vol. |
| $NF_3$ | 0.1339% vol. |
| $SF_6$ | 0.0406% vol. |
| $N_2$ | 99.58739% vol. |

Example 6

Under the same conditions as in Example 2, a feed stream comprising 1.00% vol. $C_2F_6$, 0.2% $CF_4$, and 98.9% nitrogen at a pressure of 213,315 Pascal, a temperature of 20° C. and a flowrate of 6,366 grams/min. is sent on the same membrane as in Example 1, said membrane being connected to a vacuum swing adsorption system (VSA) with a switching time of 15 min. The non-permeate (concentrated) stream from the membrane comprises:

| | |
|---|---|
| $C_2F_6$ | 74.2% wt. |
| $CF_4$ | 10.8% wt. |
| $N_2$ | 15.1% wt. |

At the same temperature and pressure than the feed stream, but at a flowrate of 84 grams/min.

The permeate stream from the membrane comprises:

| | |
|---|---|
| $C_2F_6$ | 0.001% wt. |
| $CF_4$ | 0.014% wt. |
| $N_2$ | 99.985% wt. |

The VSA non-adsorbed stream comprises:

| | |
|---|---|
| $C_2F_6$ | 94.9% wt. |
| $CF_4$ | 5.1% wt. |

The VSA adsorbed stream comprises:

| | |
|---|---|
| $CF_4$ | 30.9% wt. |
| $N_2$ | 69.1% wt. |

Example 7

A system of the invention was used to recover PFCs from an effluent stream from a semiconductor tool. A first membrane separation unit included three hollow fiber bundles, while a second membrane separation unit included only one hollow fiber bundle. Each hollow fiber bundle was equal in surface area; thus the first membrane unit provided three times the surface area for mass transfer than did the first bundle. Each bundle also used the hollow fibers described in Example 1. A feed stream comprising 2083 ppm $C_2F_6$, 595 ppm $CF_4$, and balance nitrogen, at a pressure of about 540 kiloPascal, a temperature of 305 K (32° C.) and a flowrate of 201 scfh, or 95 sl/m (standard liter per minute) was fed on the feed side of a polyimide membrane made according to U.S. Pat. No. 5,085,676. The PFC material balance indicated that the PFC flow in the feed was about 0.4590 scfh, or about 0.217 sl/m.; the product (non-permeate stream from the second membrane unit) had a PFC concentration of about 64.7%, and a nitrogen concentration of about 35.3%. The PFC recovered in the non-permeate from the second membrane was about 0.457 scfh, or 0.216 sl/m, for a PFC recovery of about 99.5%.

Further modifications to the invention will be apparent to those skilled in the art, and the scope of the following claims are not intended to be unfairly limited by the foregoing description.

What is claimed is:

1. A process to recover at least one perfluorocompound gas from a gas mixture, comprising the steps of
   a) providing a gas mixture comprising at least one perfluorocompound gas and at least one carrier gas, said gas mixture being at a first pressure and a first temperature;
   b) providing a first membrane having a feed side and a permeate side and exhibiting preferential permeation of the carrier gas, having selectivity SEL, defined as $D_c S_c / D_p S_p$ greater than 1.0, wherein,
   $D_p$ is the mobility selectivity of a perfluoro compound gas
   $S_p$ is the solubility selectivity of the perfluoro compound gas
   $D_c$ is the mobility selectivity of a carrier gas
   $S_c$ is the solubility selectivity of the carrier gas;
   c) contacting the feed side of said membrane with said gas mixture;
   d) withdrawing from the feed side of said membrane as a first non-permeate stream at a pressure which is substantially equal to said first pressure a concentrated gas mixture comprising essentially the at least one perfluorocompound gas, and
   e) withdrawing from the permeate side of said membrane as a first permeate stream a depleted gas mixture consisting essentially of the at least one carrier gas.

2. The process according to claim 1 wherein the selectivity ratio "SEL," is between about 5 and about 1,000 for any of said at least one carrier gas to any of said at least one perfluorocompound gas.

3. Process in accordance with claim 1, wherein said first pressure is supplied by compressing said gas mixture with a compressor.

4. Process in accordance with claim 3, wherein said compressor is oil-free and sealed.

5. Process in accordance with claim 3, wherein said gas mixture is treated prior to compression to remove compounds harmful to the compressor.

6. A process according to claim 1, wherein said gas mixture is treated by a pretreatment process prior to entry to the feed side of the first membrane to substantially remove species harmful for the membrane prior to contacting the feed side of the membrane with said gas mixture.

7. Process in accordance with claim 6, wherein said pretreatment process is selected from the group consisting of plasma decomposition, thermal decomposition, catalytic decomposition, scrubbing, and adsorption.

8. Process in accordance with claim 7, wherein a waste stream from said pretreatment process is used to generate perfluorocompounds.

9. A process according to claim 1, wherein said first membrane is a size selective membrane preferential to the permeation of said at least one carrier gas.

10. A process according to claim 9, wherein the membrane is asymetric.

11. A process according to claim 9, wherein said membrane comprises a plurality of hollow fibers.

12. A process according to claim 11, wherein said feed side of the membrane comprises a bore side of each of said plurality of hollow fibers, while the permeate side is an outside of each hollow fiber.

13. A process according to claim 9, wherein the membrane is a glassy polymer made of at least one polymer selected from the group consisting of polyimides, polyamides, polyamides-imides, polyesters, polycarbonates, polysulfones, polyethersulfone, alkyl substituted aromatic polyesters, cellulose acetate, fluorinated aromatic polyimides, polyphenylene oxide, sulfonated polyphenylene oxide, polyetherethersulfones, polyetherketones, copolymers thereof, blends thereof, and substituted polymers thereof.

14. A process according to claim 9 wherein the membrane is a carbon sieve membrane.

15. A process according to claim 9 wherein the membrane is a zeolite coated or zeolite filled membrane.

16. Process in accordance with claim 1, wherein said gas mixture comprises an effluent stream from a process selected from the group consisting of etching, chemical vapor deposition, and chamber cleaning.

17. A process according to claim 1, wherein the perfluorocompound gas is selected from the group consisting of fluorocarbons, $NF_3$, $SF_6$, halogenocarbons, and mixtures thereof.

18. A process according to claim 17, wherein the non-permeate stream comprises a mixture of perfluorocompound gases selected from the group consisting of $SF_6$, $C_2F_6$, $CHF_3$, $CF_4$ and $NF_3$.

19. A process according to claim 18, wherein separation of at least one less volatile from more volatile perfluorocompound gases is made by condensation in a heat exchanger using a cooling fluid at an effective temperature and flowrate.

20. A process according to claim 1, wherein the at least one carrier gas is selected from the group consisting of Ar, $N_2$, Kr, Xe, Ne, $O_2$, He, $H_2$, CO, $CO_2$, $H_2O$ and mixtures thereof including air.

21. A process according to claim 1, wherein the membrane is hollow fiber membrane comprising a polymer core and a skin, the permeability of the polymer of the skin being lower for perfluorocompound than for nitrogen.

22. A process according to claim 1, wherein the gas mixture which is contacted with the membrane comprises less than 1% vol. of each of gaseous components which are harmful for the membrane.

23. A process according to claim 1, wherein the gas mixture which is contacted with the membrane comprises less than 10 ppm of each gaseous component which is harmful for the membrane.

24. A process according to claim 1, wherein the gas mixture, which is contacted with the membrane comprises less than 1 ppm of each gaseous component which is harmful for the membrane.

25. A process according to claim 1, wherein the gas mixture prior to contacting the feed side of the membrane, is brought to a pressure which is effective for carrying out the separation of the perfluorocompound gas or gas mixture in order to recover a non-permeate stream which is concentrated in perfluorocompound species compared to the gas mixture.

26. A process according to claim 1 wherein a ratio of absolute pressure of the feed side to the permeate side is between about 2 and about 10.

27. A process according to claim 1, wherein the first pressure of the gas mixture at the feed to the membrane is between about $10^5$ Pascal to about $2.0 \times 10^7$ Pascal.

28. Process according to claim 1, wherein the depleted gas mixture is in flow communication with a low pressure side of a vacuum means.

29. A process according to claim 1, wherein at least a portion of the first non-permeate stream is sent to a feed side of a second membrane, said second membrane producing a second non-permeate stream more concentrated in perfluorocompounds than said first non-permeate stream, said process continuing through N membrane stages.

30. A process according to claim 29, wherein the number of stages N is at least 2, and wherein at least a portion of the permeate of a stage less than N is removed, and further wherein at least a portion of the permeate of a stage is recycled to the feed side of an upstream stage.

31. Process of claim 30 further comprising increasing the pressure of the portion of the permeate of a stage which is recycled prior to its contact with the upstream stage.

32. A process according to claim 30, wherein the second membrane has a selectivity ratio for carrier gas which is greater than a selectivity ratio of the first membrane.

33. A process according to claim 30, wherein the second membrane has a selectivity ratio for carrier gas which is less than a selectivity ratio of the first membrane for carrier gas.

34. A process in accordance with claim 29 wherein N ranges from 3 to 10.

35. Process in accordance with claim 29 wherein N membrane stages are present and the process is operated at a constant concentration set-point for one or more perfluorocompound gases in a non-permeate stream of stage N.

36. A process according to claim 29, wherein the second membrane has a selectivity ratio for carrier gas which is less than a selectivity ratio of the first membrane for carrier gas.

37. Process in accordance with claim 29, wherein at least a portion of a Nth nonpermeate stream from stage N is used as a sweep gas on the permeate side of any previous membrane and/or on the permeate side of membrane stage N.

38. Process in accordance with claim 29 wherein each stage is operated at a constant concentration set-point for one or more perfluorocompound gases in each stage by controlling at least one membrane operation parameter selected from the group consisting of flow rate, sweep gas rate, feed pressure, transmembrane pressure ratio, and temperature.

39. A process according to claim 1, wherein the non-permeate stream is compressed and/or cooled, and stored in storage means for further processing.

40. A process according to claim 1, wherein the gas mixture is derived from a manufacturing process and at least a portion of the first nonpermeate stream is recycled to the manufacturing process.

41. Process in accordance with claim 40, wherein the portion of the non-permeate stream which is recycled is routed to a surge tank prior to re-entering the process, or prior to being routed to storage.

42. A process according to claim 1, wherein at least one of the perfluorocompound gases of the non-permeate stream is further separated from other perfluorocompounds in said non-permeate stream.

43. A process according to claim 42, wherein at least a portion of the non-permeate stream consists essentially of $NF_3$ and $CF_4$ and is sent to an adsorption system wherein $NF_3$ is adsorbed and $CF_4$ is not.

44. A process according to claim 42, wherein at least a portion of the non-permeate stream consists essentially of $CHF_3$ and $C_2F_6$ and is contacted with an adsorbent whereby $CHF_3$ is preferentially adsorbed.

45. A process according to claim 42, wherein at least one of the perfluorocompounds is separated from the non-permeate stream in a membrane system having one or more membrane separation stages.

46. A process according to claim 1, wherein the gas mixture first temperature as it enters the membrane feed side is between about −40° C. to 120° C.

47. A process according to claim 1, wherein the gas mixture is heated to a second temperature before feeding gas mixture to the membrane, said second temperature ranging from about −40° to about 120° C.

48. A process according to claim 1, wherein the gas mixture is cooled to a second temperature before sending the gas mixture on to the membrane, said second temperature ranging from about −40° to about 120° C.

49. Process in accordance with claim 1, wherein at least a portion of the first nonpermeate stream is used as a sweep gas on the permeate side of the membrane.

50. Process in accordance with claim 1 wherein the process is operated at a constant concentration set-point for one or more perfluorocompound gases in said first non-permeate stream.

51. Process in accordance with claim 1, wherein the permeate stream is recycled to the process, or to storage.

52. Process in accordance with claim 1, wherein a plurality of like or unlike semiconductor manufacturing tools are arranged in parallel flow relationship, and each tool has a dedicated corresponding membrane separation unit, said membrane units being the same or different.

53. Process in accordance with claim 52 wherein there exists one or more spare membranes, which allow one or more membranes to be serviced or otherwise by-passed.

54. Process in accordance with claim 1, wherein at least a portion of the non-permeate stream from one or more initial membrane stages is treated to remove non-perfluorocompound gases and other materials which may be harmful to the membrane.

55. Process in accordance with claim 1, wherein said process is operated at a constant carrier gas flow rate.

56. A process to recover at least one perfluorocompound gas or gas mixture from a gas mixture flowing from a semiconductor manufacturing process, comprising the steps of:
   a) providing a first gas mixture comprising at least one perfluorocompound gas, at least one species harmful to a polymer membrane, and at least one carrier gas;
   b) providing said polymer membrane having a feed side and a permeate side;
   c) pretreating said first gas mixture to reduce the concentration of said species harmful to said polymer membrane and obtaining a treated gas mixture;
   d) contacting the feed side of said polymer membrane with said treated gas mixture;
   e) withdrawing a concentrated gas mixture comprising a higher concentration of the at least one perfluorocompound gas than in the treated gas mixture, from the feed side of the polymer membrane as a non-permeate stream at a pressure which is substantially equal to a pressure of said gas mixture; and
   f) withdrawing a permeate gas mixture from the permeate side of said polymer membrane, said permeate gas mixture enriched in carrier gas.

57. A semiconductor manufacturing system comprising:
   a) at least one reactor chamber adapted to receive a gas mixture comprising perfluorocompound gases and carrier gases, the reactor chamber having a reactor effluent gas conduit attached thereto;
   b) at least one size selective membrane separation unit having a feed side and a permeate side, said membrane being preferentially permeable to at least one carrier gas relative to at least one perfluorocompound gas, said membrane unit connected to said reactor chamber via the reactor effluent conduit, said membrane unit having a permeate vent conduit and a non-permeate conduit, and c) means to recycle at least a portion of a non-permeate stream from said membrane unit back to the at least one reactor chamber.

58. System in accordance with claim 57, further comprising treatment means in flow communication with the reactor effluent conduit and the membrane unit, said treatment means selected from the group consisting of plasma decomposition, thermal decomposition, catalytic removal, scrubbing, and adsorption.

59. System in accordance with claim 57, comprising a plurality of size selective membrane separation units arranged in series.

60. System in accordance with claim 59, wherein at least a portion of first permeate stream from a first membrane separation unit is vented in the vent conduit and at least a portion of downstream permeate stream from a downstream membrane separation unit is recycled to the feed side of an upstream membrane in the means to recycle.

61. System in accordance with claim 59, further comprising a damper or surge tank positioned in a non-permeate circuit.

62. System in accordance with claim 57, comprising a plurality of size selective membrane separation units arranged in parallel.

63. System in accordance with claim 57, wherein the membrane unit comprises a sweep gas conduit.

64. System in accordance with claim 57, further comprising means selected from the group consisting of compressor means, heat exchanger means, cryogenic pumping means, or vacuum pumping means in the non-permeate conduit, allowing a second portion of said non-permeate stream to be stored in condensed form for future use.

65. System in accordance with claim 57, further comprising a post-treatment means in flow communication with the non-permeate conduit, said posttreatment means selected from the group consisting of plasma decomposition, thermal decomposition, catalytic removal, scrubbing, and adsorption.

66. A semiconductor manufacturing system comprising:
  a) at least one reactor chamber adapted to receive a gas mixture comprising perfluorocompound gases, and carrier gases, the reactor chamber having a reactor effluent gas conduit attached thereto;
  b) compression means located in the reactor effluent conduit to compress an effluent gas from the reactor chamber,
  c) at least one membrane separation unit having a feed side and a permeate side, said membrane being permeable to at least one carrier gas and being substantially non-permeable to at least one perfluorocompound gas, said membrane unit connected to said reactor chamber via the reactor effluent conduit downstream of the compression means, said membrane unit having a permeate vent conduit and a non-permeate conduit, and said membrane having a selectivity ratio, "SEL," greater than about 1.0 for any of said at least one carrier gas relative to any of said at least one perfluorocompound gas
  wherein, $$SEL = [D_c][S_c]/[D_p][S_p]$$

wherein,
  SEL is the selectivity ratio
  $D_p$ is the mobility selectivity of a perfluoro compound gas
  $S_p$ is the solubility selectivity of the perfluoro compound gas
  $D_c$ is the mobility selectivity of a carrier gas
  $S_c$ is the solubility selectivity of the carrier gas d) means to recycle at least a portion of a non-permeate stream from said membrane unit back to the at least one reactor chamber;
  e) pretreatment means in flow communication with the reactor effluent stream-entering and the membrane unit, said pretreatment means selected from the group consisting of plasma decomposition, thermal decomposition, catalytic removal, scrubbing, and adsorption;
  f) the membrane unit comprising a sweep gas conduit in flow communication with the non-permeate conduit and the permeate side of the membrane;
  g) a damper or surge tank in flow communication with the non-permeate conduit; and
  h) a compressor, heat exchanger, cryogenic pump or vacuum pump in flow communication with the non-permeate conduit upstream of the surge tank, allowing a perfluorocarbon enriched stream to be stored in liquid form for future use.

67. A system for recovering a perfluorocompound gas from a gas mixture, the system comprising:
  a) treatment means for creating a treated gas mixture suitable for compression,
  b) a compressor for compressing the treated gas mixture to form a compressed gas mixture; and
  c) at least one glassy polymer membrane separation unit having a feed side and a permeate side, said membrane being permeable to at least one carrier gas and being substantially non-permeable to at least one perfluorocompound gas, said membrane unit connected to said compressor via a conduit, said membrane unit having a permeate vent conduit and a non-permeate conduit.

68. System in accordance with claim 67, wherein said glassy polymer membrane made of at least one polymer selected from the group consisting of polyimides, polyamides, polyamides-imides, polyesters, polycarbonates, polysulfones, polyethersulfone, alkyl substituted aromatic polyesters, cellulose acetate, fluorinated aromatic polyimides, polyphenylene oxide, sulfonated polyphenylene oxide, polyetherethersulfones, polyetherketones, copolymers thereof, blends thereof, and substituted polymers thereof.

69. System in accordance with claim 67, further including a vacuum pump in flow communication with the non-permeate conduit.

70. System in accordance with claim 67, further comprising a recovery unit for recovery of at least a portion of a non-permeate stream from said non-permeate conduit.

71. System in accordance with claim 67, further comprising a recycle conduit for recycling at least a portion of a non-permeate stream from said non-permeate conduit.

72. System in accordance with claim 67, further comprising a second membrane separation unit adapted to take as its feed at least a portion of a non-permeate stream via said non-permeate conduit.

73. System in accordance with claim 72, adapted to recycle at least a portion of the permeate stream from said second membrane unit to the feed of the first membrane unit.

74. System in accordance with claim 72, further including a third membrane separation unit adapted to take as its feed at least a portion of the permeate stream from said second membrane unit.

75. System in accordance with claim 74, wherein at least a portion of the non-permeate stream from said third membrane unit is adapted to be recycled to the feed of the first membrane unit.

76. System in accordance with claim 72 further comprising means to flow sweep gas to the permeate side of said second membrane, wherein said sweep gas comprises at least a portion of the non-permeate stream from said second membrane separation unit.

77. A system for recovering a perfluorocompound gas, the system comprising:
   a) compression means adapted to compress a gas mixture containing a carrier gas and a perfluorocompound gas;
   b) at least one size selective membrane separation unit having a feed side and a permeate side, said membrane being preferentially permeable to at least one carrier gas and being substantially non-permeable to at least one perfluorocompound gas, said membrane unit in flow communication with said compression means, a permeate vent conduit and a non-permeate conduit,
   c) means to recycle at least a portion of a non-permeate stream from said membrane unit back to a source of said gas mixture;
   d) gas treatment means positioned prior to the gas mixture entering the membrane unit, said gas treatment means selected from the group consisting of plasma decomposition, thermal decomposition, catalytic removal, scrubbing, and adsorption;
   e) the membrane unit comprising a sweep gas conduit in flow communication with the nonpermeate conduit and the permeate side of the membrane,
   f) a damper or surge tank in flow communication with the non-permeate conduit;
   g) liquefying means selected from the group consisting of a compressor, heat exchanger, cryogenic pump and a vacuum pump, in flow communication with the non-permeate conduit, allowing a perfluorocarbon enriched stream to be stored in condensed form for future use.

* * * * *

UNITED STATES PATENT AND TRADEMARK OFFICE
CERTIFICATE OF CORRECTION

PATENT NO. : 5,858,065
DATED : January 12, 1999
INVENTOR(S) : Yao-En LI, et al.

It is certified that error appears in the above-identified patent and that said Letters Patent is hereby corrected as shown below:

Column 1, line 8, after "1996" insert --, which is a continuation-in-part of copending application Serial No. 08/503,325, filed July 17, 1995 (now abandoned)--.

Signed and Sealed this

Twenty-third Day of March, 1999

Attest:

Q. TODD DICKINSON

*Attesting Officer*     *Acting Commissioner of Patents and Trademarks*